US006231516B1

(12) United States Patent
Keilman et al.

(10) Patent No.: US 6,231,516 B1
(45) Date of Patent: *May 15, 2001

(54) ENDOLUMINAL IMPLANT WITH THERAPEUTIC AND DIAGNOSTIC CAPABILITY

(75) Inventors: George W. Keilman, Woodinville, WA (US); George E. Cimochowski, Dallas, PA (US)

(73) Assignee: VacuSense, Inc., Woodinville, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/028,154

(22) Filed: Feb. 23, 1998

Related U.S. Application Data

(63) Continuation-in-part of application No. 08/949,413, filed on Oct. 4, 1997, now Pat. No. 5,807,258, which is a continuation-in-part of application No. 08/978,038, filed on Nov. 25, 1997, now Pat. No. 5,967,986.

(51) Int. Cl.$^7$ .......................................................... A61B 5/02

(52) U.S. Cl. ........................................... 600/485; 600/481

(58) Field of Search ...................................... 600/300, 317, 600/479, 481–488, 500, 504–506, 454; 604/49–53; 607/115–116, 154–155

(56) References Cited

U.S. PATENT DOCUMENTS

| | | | |
|---|---|---|---|
| 4,020,830 | 5/1977 | Johnson | 128/2 E |
| 4,218,298 | 8/1980 | Shimada et al. | 204/195 M |
| 4,331,654 | 5/1982 | Morris | 424/38 |
| 4,383,529 | 5/1983 | Webster | 604/20 |
| 4,411,648 | 10/1983 | Davis et al. | 604/21 |
| 4,416,274 | 11/1983 | Jacobsen et al. | 604/20 |
| 4,484,569 | 11/1984 | Driller et al. | 128/660 |

(List continued on next page.)

OTHER PUBLICATIONS

Pethig, R., Dielectric and Electronic Properties of Biological Materials, Wiley Press, Chichester, 1979, Chapter 7, "Biological Membranes and Tissue," pp. 207–243.

Knutti et al., "Integrated Circuit Implantable Telemetry Systems," *Eng. In Med. and Bio. Magazine*, 2(1):47–50, Mar. 1983.

Umemura et al., "Sonochemical Activation of Hematoporphyrin: A Potential Modality For Cancer Treatment," in *Ultrasonics Symposium Proceedings, IEEE*, 1989, pp. 955–960.

Zierhofer, C. M. and E. S. Hochmair, "High–Efficiency Coupling–Insensitive Transcutaneous Power and Data Transmission Via An Inductive Link," *IEEE Trans. Biomed. Eng.*, 37(7):716–722, Jul. 1990.

Harrison et al., "Effect of Ultrasonic Exposure Time And Burst Frequency On The enhancement Of Chemotherapy By Low–Level Ultrasound," in *IEEE Ultrasonics Symposium Proceedings*, 1992, pp. 1245–1248.

Jeffers et al., "Enhanced Cytotoxicity Of Dimethylformamide By Ultrasound In Vitro," in *IEEE Ultrasonics Symposium Proceedings*, 1992, pp. 1241–1244.

Umemura et al., "Sonodynamic Approach To Tumor Treatment," in *IEEE Ultrasonics Symposium Proceedings*, vol. 2, Tucson, Arizona, Oct. 20–23, 1992, pp. 1231–1240.

(List continued on next page.)

*Primary Examiner*—Cary O'Connor
*Assistant Examiner*—Michael Astorino
(74) *Attorney, Agent, or Firm*—Seed IP Law Group PLLC

(57) ABSTRACT

An apparatus includes an endoluminal implant, a RF coupling coil coupled to the endoluminal implant and a therapeutic transducer electrically coupled to the RF coupling coil and physically coupled to the endoluminal implant. The RF coupling coil supplies electrical power to the therapeutic transducer. The therapeutic transducer has a capability for delivering therapeutic energy to a lumen disposed within the endoluminal implant in response to signals coupled via the RF coupling coil.

46 Claims, 14 Drawing Sheets

U.S. PATENT DOCUMENTS

| | | | |
|---|---|---|---|
| 4,558,690 | 12/1985 | Joyce | 128/1 R |
| 4,652,257 | 3/1987 | Chang | 604/52 |
| 4,689,986 | 9/1987 | Carson et al. | 73/19 |
| 4,935,345 | 6/1990 | Guilbeau et al. | 435/14 |
| 5,016,615 | 5/1991 | Driller et al. | 128/24 A |
| 5,267,985 | 12/1993 | Shimada et al. | 604/290 |
| 5,277,191 | 1/1994 | Hughes | 128/713 |
| 5,445,608 | 8/1995 | Chen et al. | 604/20 |
| 5,490,840 | 2/1996 | Uzgiris et al. | 604/22 |
| 5,499,971 * | 3/1996 | Shapland et al. | |
| 5,694,936 | 12/1997 | Fujimoto et al. | 128/660.03 |
| 5,749,914 * | 5/1998 | Janssen. | |
| 5,807,258 * | 9/1998 | Cimochowski et al. | |
| 5,810,871 * | 9/1998 | Tuckey et al. | |
| 5,833,603 * | 11/1998 | Kovacs et al. | |
| B1 4,020,830 | 9/1984 | Johnson et al. | 128/635 |

OTHER PUBLICATIONS

Erickson, Katherine A. and Peter Wilding, "Evaluation of a Novel Point–Of–Care System, The i–STAT Portable Clinical Analyzer," *Clinical Chem.* 39(2):283–287, 1993.

Hetke et al., "Silicon Ribbon Cables For Chronically Implantable Microelectrode Arrays," *IEEE Trans. Biomed. Eng.*, 41(4):314–321, Apr. 1994.

Shults et al., A Telemetry–Instrumentation System For Monitoring Multiple Subcutaneously Implanted Glucose Sensors, *IEEE Trans. Biomed. Eng* 41(10):937–942, Oct. 1994.

Andle, J. C. and J. F. Vetelino, "Acoustic Wave Biosensors," in *IEEE Ultrasonics Symposium*, Jun. 1995, pp. 451–460.

Welsh et al., "Iontophoretic Drug Delivery System," *Semin. Intervent. Cardiol.* 1:40–42, 1996.

Wilensky, Robert L. and Keith L. March, "Microspheres," *Semin. Intervent. Cardiol.* 1:48–50, 1996.

Umemura et al., "Effect of Second–Harmonic Phase On Producing Sonodynamic Tissue Damage," in *IEEE Ultrasonics Symposium Proceedings*, vol. 2, San Antonio, Texas, Nov. 3–6, 1996, pp. 1313–1318.

"Technical Report: Drug And Gene Delivery," *ImaRx Pharmaceutical Corp.*, Jul. 1, 1997.

Tachibana, K. and Tachibana, S., "Prototype Therapeutic Ultrasound Emitting Catheter For Accelerating Thrombolysis," *J. Ultrasound Med.* 16:529–535, 1997.

Pethig, R., *Dielectric and Electronic Properties of Biological Materials*, Wiley Press, Chicester, 1979, Chapter 7, "Biological Membranes and Tissue", pp. 207–243.

Knutti et al., "Integrated Circuit Implantable Telemetry Systems", *Eng. In Med. and Biol. Magazine*, 2(1): 47–50, Mar. 1983.

* cited by examiner

ENDOLUMINAL IMPLANT WITH THERAPEUTIC AND DIAGNOSTIC CAPABILITY

CROSS-REFERENCE TO RELATED APPLICATION

This application is a continuation-in-part of application No. 08/949,413 filed Oct. 14, 1997, now issued as U.S. Pat. No. 5,807,258 and a continuation-in-part of application No. 08/978,038 filed Nov. 25, 1997, now issued as U.S. Pat. No. 5,967,986.

TECHNICAL FIELD

This invention relates generally to implantable devices, and, more particularly, to implantable medical devices having therapeutic or diagnostic functions within a lumen of an endoluminal implant such as a stent or other type of endovascular conduit, and methods related to such implantable medical devices.

BACKGROUND OF THE INVENTION

In the 1970s, the technique of percutaneous transluminal coronary angioplasty (PTCA) was developed for the treatment of atherosclerosis. Atherosclerosis is the build-up of fatty deposits or plaque on the inner walls of a patient's arteries; these lesions decrease the effective size of the artery lumen and limit blood flow through the artery, prospectively causing a myocardial infarction or heart attack if the lesions occur in coronary arteries that supply oxygenated blood to the heart muscles. In the angioplasty procedure, a guide wire is inserted into the femoral artery and is passed through the aorta into the diseased coronary artery. A catheter having a balloon attached to its distal end is advanced along the guide wire to a point where the sclerotic lesions limit blood flow through the coronary artery. The balloon is then inflated, compressing the lesions radially outward against the wall of the artery and substantially increasing the size of its internal lumen, to improve blood circulation through the artery.

Increasingly, stents are being used in place of or in addition to PTCA for treatment of atherosclerosis, with the intent of minimizing the need to repeatedly open an atherosclerotic artery. Although a number of different designs for stents exist in the prior art, all are generally configured as elongate cylindrical structures that are provided in a first state and can assume a second, different state, with the second state having a substantially greater diameter than the first state. A stent is implanted in a patient using an appropriate delivery system for the type of stent being implaced within the patient's arterial system. There are two basic types of stents—those that are expanded radially outward due to the force from an inflated angioplasty type balloon, such as the Palmaz-Schatz stent, the Gianturco-Roubin stent and the Strecker stent, and those that are self expanding, such as the Maass double helix spiral stent, the Nitinol stent (made of nickel titanium memory alloy), the Gianturco stent and the Wallstent. Problems with the Maass double helix spiral stent and the Nitinol stent have limited their use.

Stents are sometimes used following a PTCA procedure if the artery is totally occluded or if the lesions have occluded a previously placed surgical graft. Typically, a stent constrained within an introducer sheath is advanced to a site within the patient's artery through a guide catheter. For the balloon expanded type, after the introducer sheath is retracted, a balloon disposed inside the stent is inflated to a pressure ranging from about six to ten atmospheres. The force produced by the inflated balloon expands the stent radially outward beyond its elastic limit, stretching the vessel and compressing the lesion to the inner wall of the vessel. A self expanding stent expands due to spring force following its implacement in the artery, after a restraining sheath is retracted from the compressed stent, or in the case of the Nitinol version, the stent assumes its expanded memory state after being warmed above the transition temperature of the Nitinol alloy (e.g., above 30° C.). Following the expansion process, when the balloon catheter is used, the balloon is removed from inside the stent and the catheter and other delivery apparatus is withdrawn. The lumen through the vessel is then substantially increased, improving blood flow.

After a stent or other endoluminal device is implanted, a clinical examination and either an angiography or an ultrasonic morphological procedure is performed to evaluate the success of the stent emplacement procedure in opening the diseased artery or vessel. These tests are typically repeated periodically, e.g., at six-month intervals, since restenosis of the artery may occur. Due to the nature of the tests, the results of the procedure can only be determined qualitatively, but not quantitatively, with any degree of accuracy or precision. It would clearly be preferable to monitor the flow of blood through the stent after its implacement in a vessel, both immediately following the treatment for the stenosis and thereafter, either periodically or on a continuous basis. Measurements of volumetric rate and/or flow velocity of the blood through the stent would enable a medical practitioner to much more accurately assess the condition of the stent and of the artery in which the stent is implanted. Currently, no prior art mechanism is available that is implantable inside a blood vessel for monitoring blood flow conditions through a stent.

Following stent implantation, it is difficult to monitor the condition of the affected area. Stents often fail after a period of time and for a variety of reasons. Several of the causal mechanisms are amenable to drug treatment. It is highly desirable in at least some of these cases to localize the drug treatment to the site of the graft or surgery. For example, when thrombus forms in a given area, thrombolytic drugs are capable of providing significant assistance in resolving the thrombosis, but may present problems such as hemorrhaging, if they also act in other portions of the patient's body.

SUMMARY OF THE INVENTION

The present invention provides a capability for including a therapeutic transducer together with an endoluminal implant such as a stent or stent graft. Therapeutic transducers may include ultrasonic, magnetic, iontophoretic, heating or optical devices, which may permit localized drug delivery or localized drug activation. Provision is made for delivering energy to the implanted transducers and for coupling signals to or from the implanted transducers. The present invention also permits inclusion of diagnostic transducers together with the endoluminal implant and allows signals to be transmitted from the diagnostic transducers to an area outside of the patient's body.

The present invention can allow steps that may be taken to restore full fluid flow through, e.g., a stent that is becoming restricted. In these cases, it is desirable to initiate treatment before the problem proceeds too far to be corrected without stent replacement or further PTCA treatment. Clearly, it would be preferable to be able to monitor the condition of a stent without resorting to invasive surgical procedures and without prescribing medication that may not be necessary, so that the useful life of the stent may be extended, problems associated stent failure avoided and so that medications are only prescribed when required by the known condition of the stent and associated vasculature.

Other advantages that may be realized via embodiments of the present invention including monitoring of other parameters measurable within a stent or other type of endoluminal implant using one or more appropriate sensors or transducers according to embodiments of the present invention. For example, monitoring pressure at the distal and proximal ends of the lumen in the implant and determining the differential pressure can provide an indication of fluid velocity through the lumen. Temperature can also be used to monitor fluid flow by applying heat to the fluid within the lumen and monitoring the rate at which the temperature of the fluid decreases as the fluid flows through the lumen of the implant. Integrated circuit (IC) transducers are currently known and available for sensing the levels of many different types of biochemical substances, such as glucose, potassium, sodium, chloride ions and insulin. Any of these IC sensors could be provided in an endoluminal implant to monitor these parameters.

Since it is impractical to pass a conductor through the wall of an artery or vessel for long periods of time, use of a conventional sensor that produces signals indicative of flow through a stent, which must be conveyed through a conductor that extends through the wall of the vessel and outside the patient's body, is not a practical solution to this problem. Also, any active flow indicative sensor must be energized with electrical power. Again, it is not practical to supply power to such a sensor through any conductor that perforates the vessel wall or that passes outside the patient's body.

In addition to stents, the generic term endoluminal implant encompasses stent grafts, which are also sometimes referred to as "spring grafts." A stent graft is a combination of a stent and a synthetic graft is endoluminally implanted at a desired point in a vessel. Helically coiled wires comprising the stent are attached to the ends of the synthetic graft and are used to hold the graft in position. Sometimes, hooks are provided on the stent to ensure that the graft remains in the desired position within the vessel. Clearly, it is advantageous to monitor the status of flow and other parameters through a stent graft, just as noted above in regard to a stent.

Endoluminal implants are used in other body passages in addition to blood vessels. For example, they are sometimes used to maintain an open lumen through the urethra, or through the cervix. A stent placed adjacent to an enlarged prostate gland can prevent the prostate from blocking the flow of urine through the urethra. Tracheal and esophageal implants are further examples of endoluminal implants. In these and other uses of endoluminal implants, provision for monitoring parameters related to the status of flow and other conditions in the patient's body is desirable. Information provided by monitoring such parameters, and localized drug delivery or drug activation, can enable more effective medical treatment of a patient through use of embodiments of the present invention.

Another advantage that may be realized through practice of embodiments of the present invention is to be able to activate a therapeutic device on the stent or stent graft that would allow the physician to activate drugs known to be effective in preventing further tissue growth within the stent or stent graft in situations where it is determined that tissue ingrowth is threatening the viability of a stent or stent graft. Again, the therapeutic device should be able to be supplied with electrical power from time to time from a location outside the patient's body.

Yet another advantage that may be realized through practice of the present invention is the treatment of tumors or organs that are downstream of the blood vessel that includes a stent that is coupled to a transducer. The transducer may be remotely activated to facilitate localized drug delivery or to provide other therapeutic benefits.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE INVENTION

Figure 1:
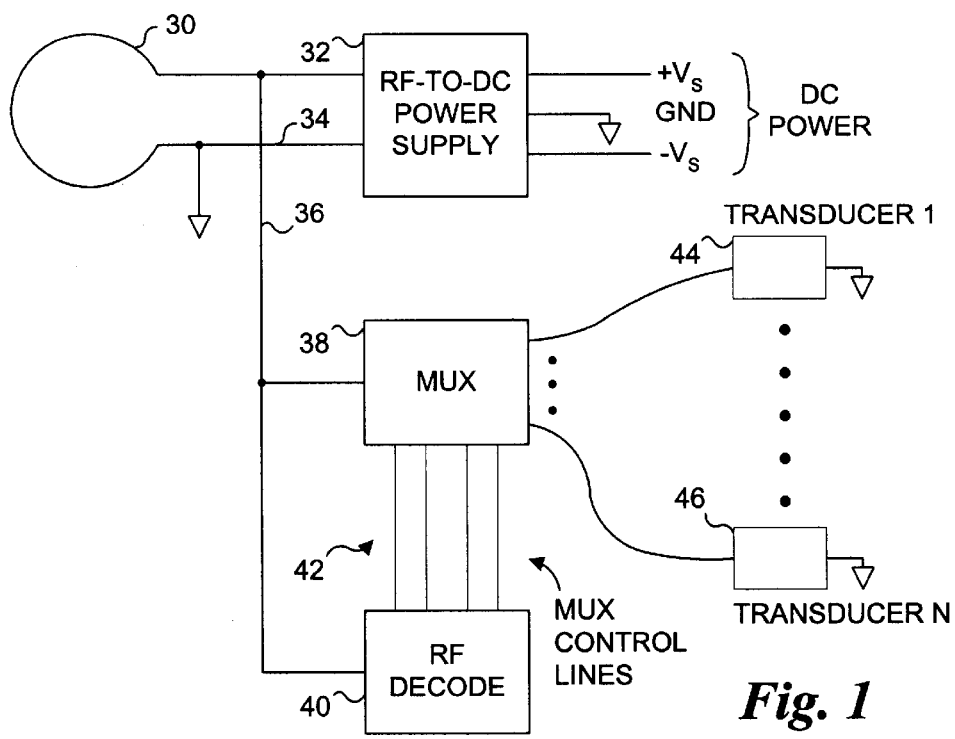
FIG. 1 is a block diagram according to the invention showing a first embodiment of an implantable electronic circuit for coupling electrical signals to or from a selected transducer of a plurality of transducers.

The present invention is employed for providing therapeutic functions proximate to an endoluminal implant. As used herein and in the claims that follow, the term endoluminal implant broadly encompasses stents, stent grafts (sometimes referred to as "spring grafts") and other types of devices that are inserted into a lumen or body passage and moved to a desired site to provide a structural benefit to the lumen. To simplify the disclosure of the present invention, most of the following discussion is directed to embodiments comprising a stent.

In one embodiment, parameters are monitored via implanted diagnostic transducers, where the monitored parameters are directed to determining the status of the fluid flow through the endoluminal implant, and therapeutic transducers may be activated in response to the data collected from the implanted diagnostic transducers. For example, the rate or velocity of fluid flow through a body passage in which the stent has been positioned can be monitored to determine the extent of tissue growth or fatty deposits in a blood vessel in which the stent has been implanted to treat atherosclerosis. By monitoring these parameters, which are indicative of blood flow through the lumen of the stent and the blood vessel in which it is implanted, a medical practitioner can evaluate the need for further treatment or determine whether restenosis has occurred, and can locally activate drugs to control restenosis when it is determined to have occurred. This may be possible without additional surgery and without some of the complications associated with systemic administration of drugs. Moreover, other physical and biological parameters can be monitored using one or more appropriate sensors attached to a stent.

When implanted therapeutic transducers are to be activated for an extended period of time or following an extended delay, the stent will likely need to receive electrical power from an external source to energize the implantable electronic circuitry used to activate the implanted therapeutic transducers. Similarly, when the status of fluid flow through a stent that has been implanted in a patient's vascular system (or some other parameter that is sensed proximate the stent) is to be monitored for an extended period or following an extended delay, the implanted circuitry associated with the stent will likely need to receive electrical power from an external source. This power may also be needed to convey data indicating the status of fluid flow (or other parameter) from the implanted stent to a monitoring device that is disposed outside the patient's body. In many cases, it may be desirable to monitor one or more parameters at multiple stents or at multiple locations on a single stent, or to provide therapeutic functions at more than one stent or to multiple locations within or associated with one stent. Thus, the specific transducer employed to provide a therapeutic function or transducer or sensor employed to monitor a desired parameter must be selectable so that the data signal indicating the parameter can be transmitted outside the patient's body. However, in some cases, only a single transducer (which may be operable without any implanted control electronics) may be required to provide a therapeutic function or to monitor a parameter such as fluid volumetric flow or velocity, which is indicative of the internal condition of the stent and of the blood vessel in which it is implanted.

FIG. 1 illustrates a first embodiment of an implantable electronic circuit for providing one or more therapeutic functions or for monitoring one or more parameters, applicable to the situation in which n transducers 44–46 are included on one or more stents implanted in the patient's body. Variations of the implantable electronic circuit shown in FIG. 1 are discussed below to accommodate specific conditions. In addition, other embodiments of implantable electronic circuits are illustrated in FIGS. 2 through 6. These embodiments, like that of FIG. 1, are useful for providing power to transducers that provide therapeutic functions, e.g., that activate drugs or that assist in localized drug delivery, or that monitor fluid flow or velocity through a stent and also for transmitting data signals from the transducers to locations outside a patient's body, e.g., to an external remote monitoring console. Some of these implantable electronic circuits are better suited for certain types of therapy or measurements than others, and again, variations in the implantable electronic circuits are discussed below, where appropriate, to explain these distinctions. Examples of implantable telemetry systems are discussed in *A Telemetry-Instrumentation System For Monitoring Multiple Subcutaneously Implanted Glucose Sensors* by M. C. Shults et al., IEEE Trans. Biomed. Eng., Vol. 41, No. 10, October 1994, pp. 937–942 and in *Integrated Circuit Implantable Telemetry Systems* by J. W. Knutti et al., Eng. in Med. and Bio. Magazine, March 1983, pp. 47–50.

Each of the implantable electronic circuits shown in FIGS. 1 through 6 are intended to be implanted within the patient's body and left in place at least during the period in which a therapeutic function may be needed or the flow conditions through one or more stents or other parameters are monitored. Although separate functional blocks are illustrated for different components of the implantable electronic circuits in these Figures, any of the implantable electronic circuits can be implemented in one or more application specific integrated circuits (ASICs) to minimize size, which is particularly important when the implantable electronic circuits are integral with a stent. The implantable electronic circuits can be either included within the wall of a stent, or may be simply implanted adjacent to blood vessel(s) in which the stent(s) is/are disposed. However, if not integral with the stent, the implantable electronic circuits must be electromagnetically coupled to the transducers, since it is impractical to extend any conductor through a wall of the blood vessel in which a stent is implanted, to couple to circuitry disposed outside the blood vessel. Therefore, in some embodiments, the implantable electronic circuits are integral with the stent so that they are implanted, together with the stent, inside the blood vessel.

Each of the implantable electronic circuits shown in FIGS. 1 through 6 includes a RF coupling coil 30, which is coupled via lines 34 and 36 to a RF-to-DC power supply 32. In one embodiment, the RF coupling coil 30 is part of the expandable structure of the stent body or may instead be added to a stent, for example, by threading an insulated wire through the expandable wall of a stent. In some embodiments, the RF coupling coil 30 comprises a helical coil or saddle-shaped coil, as explained in greater detail below. The RF-to-DC power supply 32 rectifies and filters a RF excitation signal supplied from an external source to the RF coupling coil 30, providing an appropriate voltage DC power signal for the other components of the implantable electronic circuits illustrated in these Figures. In the simplest case, the RF-to-DC power supply 32 would only require rectifiers and filters as appropriate to provide any needed positive and negative supply voltages, $+V_S$ and $-V_S$.

However, it is also contemplated that the RF-to-DC power supply 32 may provide for a DC-to-DC conversion capability in the event that the electromagnetic signal coupled into the RF coupling coil 30 is too weak to provide the required level of DC voltage for any component. This conversion capability would increase the lower voltage produced by the direct coupling of the external RF excitation signal received by the RF coupling coil 30, to a higher DC voltage. Details of the RF-to-DC power supply 32 are not shown, since such devices are conventional. It is also contemplated that it may be necessary to limit the maximum amplitude of the RF input signal to the RF-to-DC power supply 32 to protect it or so that excessive DC supply voltages are not provided to the other components.

Alternatively, each component that must be provided with a limited DC voltage supply may include a voltage limiting component, such as a zener diode or voltage regulator (neither shown). In another embodiment, the RF coupling coil 30 and the RF-to-DC power supply 32 of FIGS. 1 through 6 may be replaced by a hard-wired connection to supply DC or AC power in applications where the implant is needed for a relatively short duration, where the inconvenience of the cables supplying the power is tolerable and the risk of infection is manageable. An example of a hard-wired transcutaneous connection for chronic implants is described in *Silicon Ribbon Cables For Chronically Implantable Microelectrode Arrays* by J. F. Hetke et al., IEEE Trans. Biomed. Eng., Vol. 41, No. 4, April 1994, pp. 314–321.

The RF-to-DC power supply 32 may include a battery or a capacitor for storing energy so that it need not be energized when providing a therapeutic function or monitoring the flow status, or at least, should include sufficient storage capability for at least one cycle of receiving energy and transmitting data relating to the parameter being monitored. Neither a battery nor power storage capacitor are illustrated in the Figures, since they are conventional also.

Implantable electronic systems using battery power may only require the ability to receive data and control signals and may include the ability to transmit signals. As a result, they do not necessarily require access to the skin, which access facilitates efficient coupling of power signals. A battery-powered system may result in a very compact implantable system. Alternatively, a battery-powered system that also is capable of recharging the battery via power signals coupled through an implanted coil can permit continuing treatment without requiring that a physician be present throughout the treatment or requiring the patient to be in the medical facility.

Figure 2:
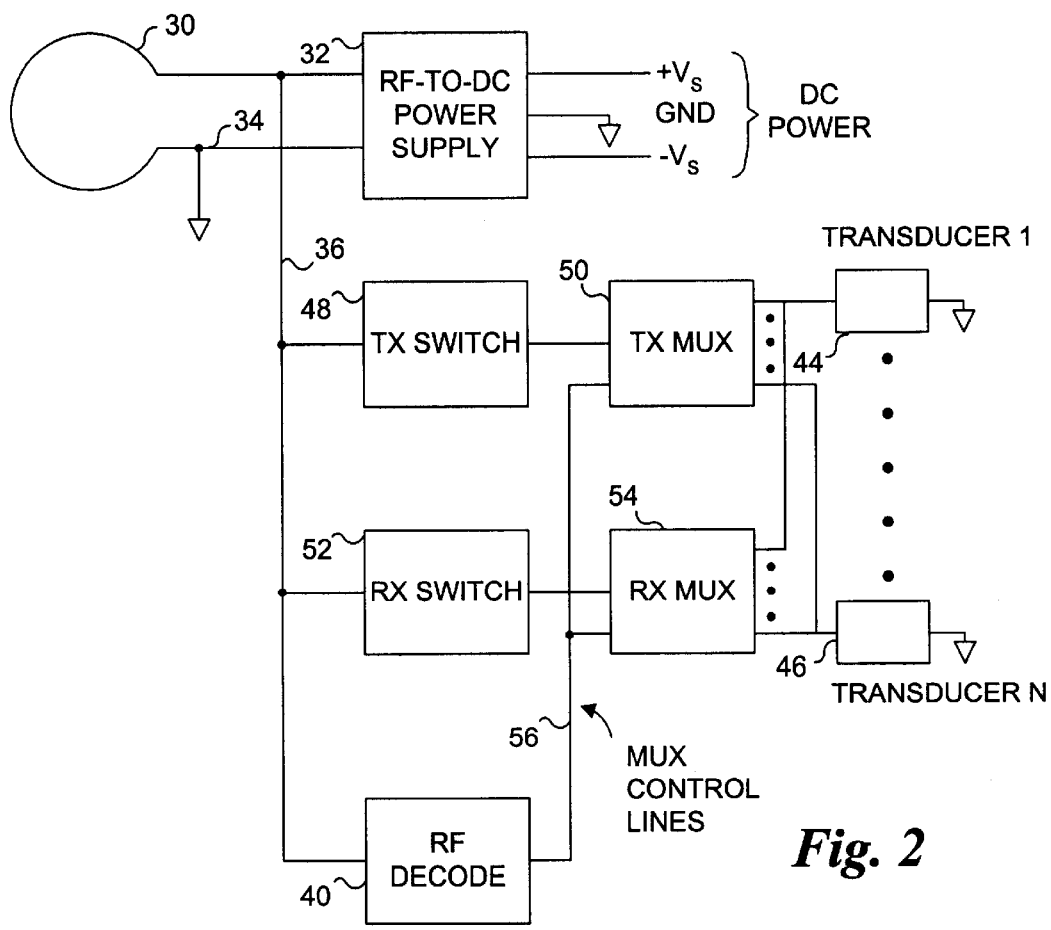
FIG. 2 is a block diagram of a second embodiment of an implantable electronic circuit for coupling electrical signals to or from a transducer using separate multiplexers for transmit and receive functions.
Figure 3:
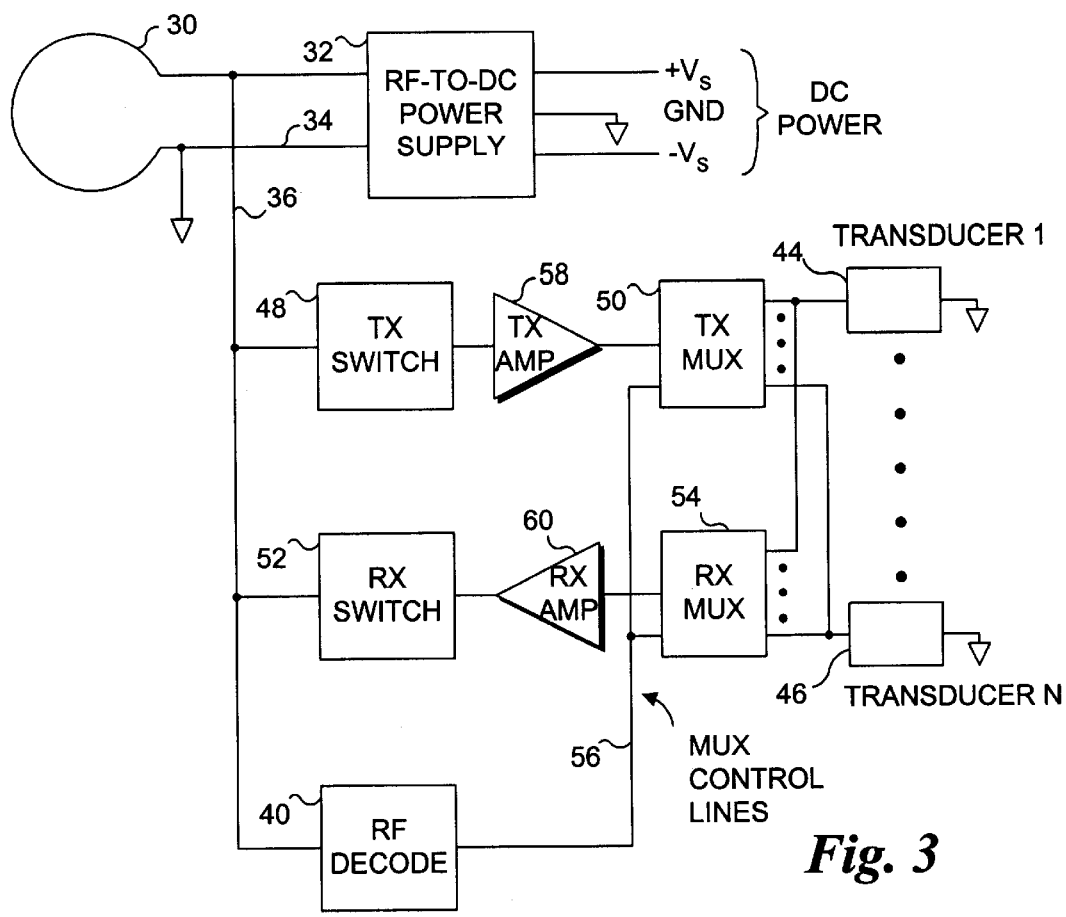
FIG. 3 is a block diagram of a third embodiment of an implantable electronic circuit for coupling electrical signals to or from a transducer using separate multiplexers and amplifiers for transmit and receive functions.

An element that is common to each of the implantable electronic circuits shown in FIGS. 1 through 3 is a RF decode section 40, which is used for generating control signals that are responsive to information encoded in the external RF excitation signal received by the RF coupling coil 30. This information can be superimposed on the RF excitation signal, e.g., by amplitude or frequency modulating the signal.

In regard to the implantable electronic circuits shown in FIGS. 1 through 3, when used for monitoring fluid velocity or flow, the RF excitation frequency is the same as the frequency used to provide energy for therapeutic functions (e.g., localized drug activation) or to excite a selected ultrasonic transducer to produce an ultrasonic wave that propagates through a lumen of the stent being monitored and for conveying data from the transducer 44–46 that receives the ultrasonic waves. This approach generally simplifies the implantable electronic circuitry but may not provide optimal performance.

Figure 4:
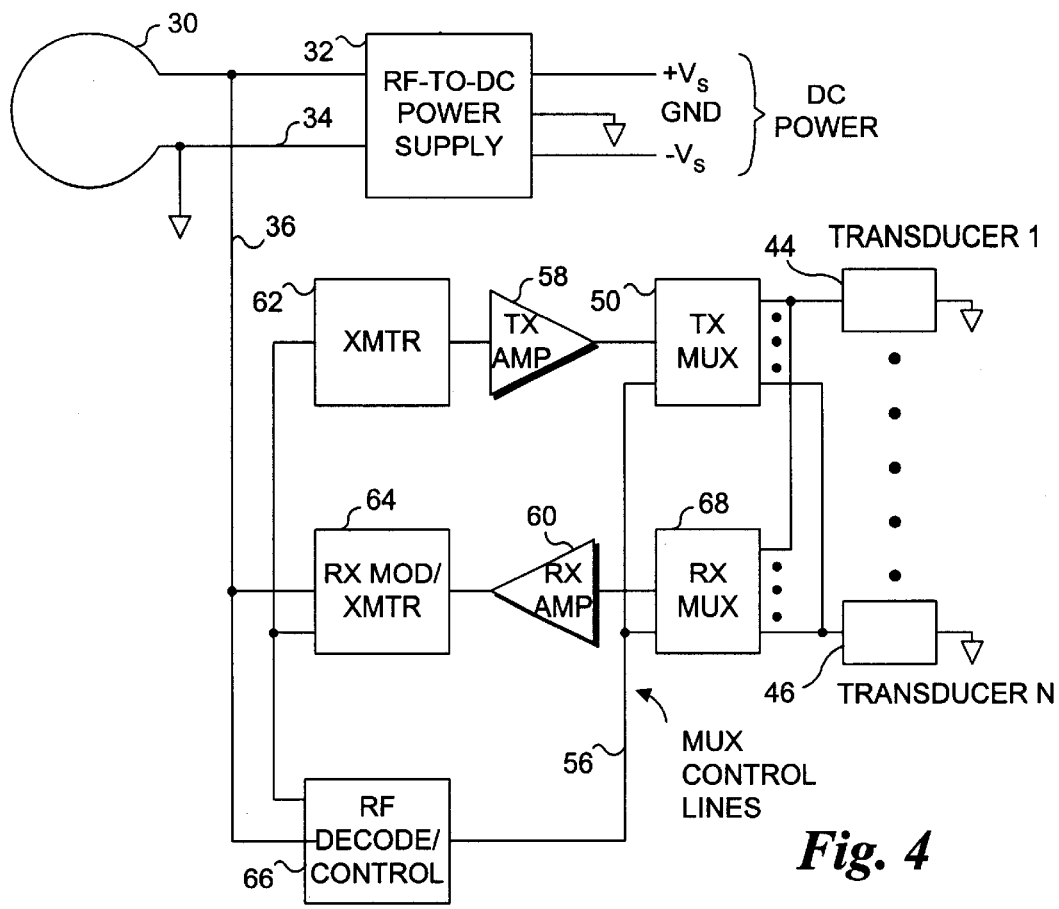
FIG. 4 is a block diagram of a fourth embodiment of an implantable electronic circuit for coupling electrical signals to or from a transducer that employs a local transmitter to excite a selected transducer, and a modulator/transmitter for transmitting signals from the transducers.
Figure 5:
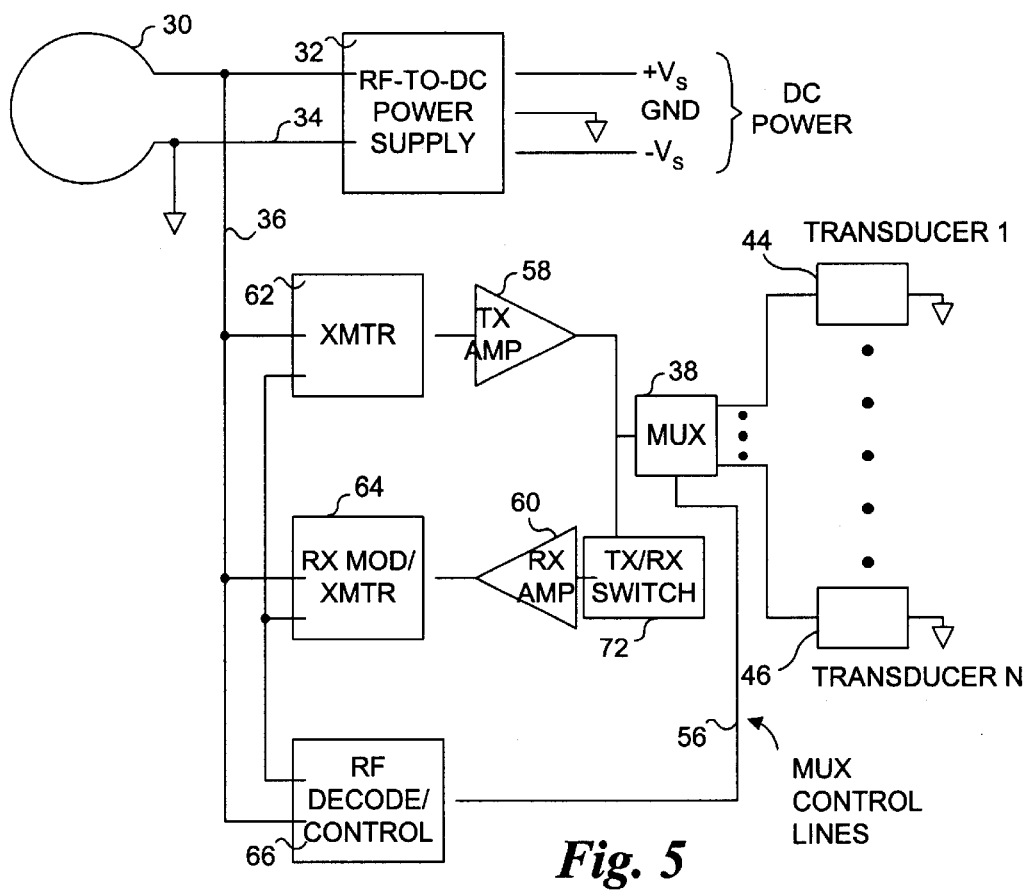
FIG. 5 is a block diagram of a fifth embodiment of an implantable electronic circuit for coupling electrical signals to or from a transducer, where one transducer is selected for transmitting and receiving, and a modulator/transmitter is used for transmitting the signal produced by the receiving transducer.

Therefore, FIGS. 4 and 5 disclose implantable electronic circuitry in which the RF excitation frequency used to provide power to the RF-to-DC power supply 32 and to provide control signals to the RF decode section 40 is decoupled from the frequency that is used for exciting the transducers 44–46 and modulating any data that they provide for transmission to a point outside the patient's body. Although other types of transducers 44–46 may be employed that are energized with a RF excitation frequency, such as surface acoustic wave transducers that are used for sensing chemical substances, many transducers 44–46 only require a DC voltage to sense a desired parameter such as pressure or temperature or to provide a static magnetic field, heat or light for therapeutic purposes.

Implantable Electronic Circuits

Referring now to FIG. 1, a line 36 from the RF coupling coil 30 is coupled to a multiplexer (MUX) 38 to convey signals from a selected one of a plurality of n transducers 44–46 (which are disposed at different points on a stent) that are coupled to the MUX 38. To select the transducer 44–46 that will provide a therapeutic function or a data signal related to a parameter at a specific location on a stent, the RF decode section 40 provides a control signal to the MUX 38 through MUX control lines 42. The control signal causes the MUX 38 to select a specific transducer 44–46 that is to be excited by the RF signal received by the RF coupling coil 30 and further, causes the MUX 38 to select the transducer 44–46 that will provide the data signal for transmission outside the patient's body (or at least outside the blood vessel in which the stent is disposed) via the RF coupling coil 30.

In addition to ultrasonic transducers 44–46, the implantable electronic circuit shown in FIG. 1 can also be used in connection with pressure transducers 44–46. For ultrasonic transducers 44–46, the circuit is perhaps more applicable to the Doppler type for use in monitoring fluid velocity through a stent. If a single-vessel pulse Doppler transducer 44–46 is used, the same transducer 44–46 can be used for both transmission and reception of the ultrasonic wave, thereby eliminating the need for the MUX 38. In the event that the transducers 44–46 shown in FIG. 1 are used for transit time flow measurements, it will normally be necessary to use the MUX 38 to switch between the transducer 44–46 used for transmitting the ultrasonic wave and that used to receive the ultrasonic wave.

For a single-vessel transit time measurement, a pair of opposed transducers 44–46 that are disposed on opposite sides of the stent are typically used. In order to acquire bi-directional fluid flow data, the direction of the ultrasound wave propagation must be known, i.e., the direction in which the ultrasound wave propagates relative to the direction of fluid flow through the vessel. In this case, the MUX 38 is required. However, for single-vessel applications in which the fluid flow is in a single known direction, the transducers 44–46 that are disposed on opposite sides of the stent can be electrically coupled in parallel or in series, eliminating any requirement for the MUX 38. The RF-to-DC power supply 32 and the RF decode section 40 could also then be eliminated, since the retarded and advanced transit time signals are superimposed on the same RF waveform transmitted by the RF coupling coil 30 to a location outside the patient's body (or outside the blood vessel in which the stent is disposed, if an internal coil is implanted adjacent the blood vessel near where the stent is implanted). Although this modification to the implantable electronic circuit shown in FIG. 1 would not permit the direction of fluid flow through a stent to be determined, the retarded and advanced transit time signals interfere over time, and their interference can be used to estimate the magnitude of fluid flow through the stent.

In some applications, a single transducer 44–46 or group of transducers 44–46 may be employed, in which case the implantable electronic circuit of FIG. 1 may be simplified by coupling the transducer(s) 44–46 directly to the RF coupling coil 30 and eliminating the MUX 38. In this embodiment, the RF decode section 40 and the RF-to-DC power supply 32 are optional; when the transducer, for example, requires DC excitation or other excitation different than that which may be provided directly via the RF coupling coil 30, the RF-to-DC power supply 32 may be desirable. Similarly, some sensors may have more than one function and then the RF decode section 40 may also be desirable. Similarly, the implantable electronic circuits of FIGS. 2 through 6 may be modified to provide the desired or required functionality.

In FIG. 2, an implantable electronic circuit is shown that uses a transmit multiplexer (TX MUX) 50 and a receive multiplexer (RX MUX) 54. In addition, a transmit (TX) switch 48 and a receive (RX) switch 52 couple line 36 to the TX MUX 50 and the RX MUX 54, respectively. The RF decode section 40 responds to instructions on the signal received from outside the patient's body by producing a corresponding MUX control signal that is conveyed to the TX MUX 50 and the RX MUX 54 over MUX control lines 56 to select the desired transducers 44–46.

When ultrasonic signals are being transmitted by one of the selected transducers 44–46, the TX switch 48 couples the RF excitation signal received by the RF coupling coil 30 to the transducer 44–46 that is transmitting the ultrasonic signal, which is selected by the TX MUX 50. The TX switch 48 is set up to pass excitation signals to the selected transducer 44–46 only if the signals are above a predetermined voltage level, for example, 0.7 volts. Signals below that predetermined voltage level are blocked by the TX switch 48. Similarly, the RX switch 52 couples the transducer 44–46 selected by the RX MUX 54 to the RF coupling coil 30 and passes only signals that are below the predetermined voltage level, blocking signals above that level. Accordingly, the RF signal used to excite a first transducer 44–46 selected by the TX MUX 50 passes through the TX switch 48 and the lower amplitude signal produced by a second transducer 44–46 selected by the RX MUX 54 in response to the ultrasonic signal transmitted through the stent is conveyed through the RX MUX 54 and the RX switch 52 and transmitted outside the patient's body through the RF coupling coil 30.

The implantable electronic circuit shown in FIG. 3 is similar to that of FIG. 2, but it includes a transmit amplifier (TX AMP) 58 interposed between the TX switch 48 and the TX MUX 50, and a receive amplifier (RX AMP) 60 interposed between the RX MUX 54 and the RX switch 52. The TX AMP 58 amplifies the excitation signal applied to the transducer 44–46 selected by the TX MUX 50 for producing the ultrasonic wave that is propagated through the interior lumen of a stent. Similarly, the RX AMP 60 amplifies the signal produced by the transducer 44–46 selected by the RX MUX 54 before providing the signal to the RX switch 52 for transmission outside the patient's body (or at least, outside the blood vessel in which the stent is implanted). Again, the implantable electronic circuit shown in FIG. 3 is most applicable to transit time flow measurements and employs the same frequency for both the RF excitation signal that supplies power to the RF-to-DC power supply 32 and the signal applied to a selected one of the transducers 44–46 to generate the ultrasonic wave propagating through the stent.

Figure 6:
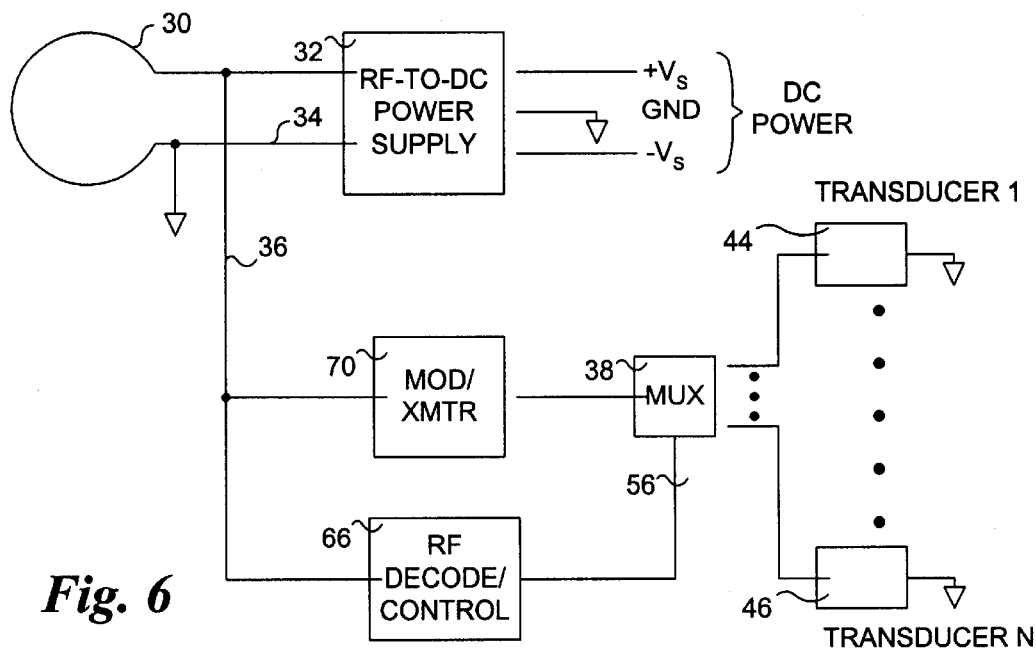
FIG. 6 is a block diagram of a sixth embodiment of an implantable electronic circuit for monitoring the status of a stent or stent graft, wherein one of a plurality of transducers is selectively coupled to a modulator/transmitter or a receiver.

In contrast to the implantable electronic circuits shown in FIGS. 1 through 3, the implantable electronic circuit shown in FIGS. 4 through 6 enables the RF excitation frequency applied to the RF-to-DC power supply 32 to be decoupled from the frequency of the signal applied to excite any selected one of the transducers 44–46. Similarly, the signal produced by the transducer 44–46 receiving ultrasonic waves propagating through the stent is at a different frequency than the RF excitation frequency applied to the RF-to-DC power supply 32. In FIG. 4, a transmitter (XMTR) 62 and a receive modulator/transmitter (RX MOD/XMTR) 64 are coupled to and controlled by a RF decode/control section 66. The RF decode/control section 66 determines when the excitation frequency is generated for application to a selected transmit transducer 44–46 and when the signal produced by the transducer selected to receive the ultrasonic wave is used for modulating the RF signal applied to the RF coupling coil 30. An advantage of this approach is that the RF power delivered to the RF coupling coil 30 is at an optimal frequency for penetration through the patient's body, thereby improving the efficacy with which the RF energy couples to a specific depth and location within the body. Another reason for using this approach is to enable selection of a particular frequency as necessary to comply with radio frequency allocation bands for medical equipment. Similarly, the frequency applied to any selected transducers 44–46 to stimulate their production of ultrasonic waves can be optimal for that purpose. Assuming that the two frequency bands, i.e., the RF excitation frequency band for the signal applied to the RF-to-DC power supply 32 and the frequency band of the signals applied to excite the transducers 44–46, are sufficiently separated, the RF power delivery can occur simultaneously with the excitation of a selected transducer 44–46 and the reception of the ultrasonic waves by another selected transducer 44–46. Accordingly, more RF power can be coupled into the system from the external source than in the implantable electronic circuits shown in FIGS. 1 through 3. In some embodiments, including those where a battery is used, the RF decode/control section 66 may also include a RF oscillator for providing the RF signals to the transducers 44–46 or for coupling signals from the transducers 44–46 to external electronic apparatus.

The control signals that are supplied to the RF decode/control section 66 via the RF coupling coil 30 can be conveyed using nearly any kind of modulation scheme, e.g., by modulating the RF excitation that powers the device, or by sending a control signal on a separate and distinct RF frequency. Also, the signals that are received from the transducer 44–46 in response to the ultrasonic wave that is propagated through the stent can be transmitted through the RF coupling coil 30 at a different frequency than the incoming excitation frequency, thereby reducing the likelihood of interference between the power supply and data signal transmission functions.

The implantable electronic circuit shown in FIG. 4 is applicable to transit time flow measurements in which pairs of transducers 44–46 are selected for transmitting and receiving the ultrasonic wave that propagates through the one or more stents on which the transducers 44–46 are installed. The RF decode/control section 66 can be employed to control the TX MUX 50 and the RX MUX 68 to interchange the transducers 44–46 used for transmission and reception of the ultrasonic wave on successive pulses. Using this technique, the direction of the ultrasonic wave propagation through the stent is changed on alternating pulses of ultrasonic waves, enabling transit time difference information to be gathered without requiring further multiplexer programming information to be transmitted between successive ultrasonic wave pulses. This approach greatly improves the data gathering efficiency of the implantable electronic circuit shown in FIG. 4 compared to the previously described implantable electronic circuits of FIGS. 1 through 3.

To further improve the implantable electronic circuit shown in FIG. 4 for use in sensing fluid velocity through a stent using a Doppler technique, the modification shown in FIG. 5 is made. In FIG. 5, a TX/RX switch 72 is added so that the implantable electronic circuit transmits and receives through the same transducer 44–46. As a result, the separate transmit 50 and receive 54 multiplexers of FIG. 4 are not required. Instead, the MUX 38 is used to select the specific transducer 44–46 for receiving the RF excitation signal produced by the XMTR 62 so that the transducer 44–46 produces an ultrasonic wave and then receives the echo from fluid flowing through the stent to produce a received data signal that is output through the RX MOD/XMTR 64. The TX/RX switch 72 prevents the signal applied by the TX AMP 58 from overdriving the input to the RX AMP 60, effectively isolating the RX AMP 60 during the time that the RF signal is applied to the transducer 44–46 to excite it so that it produces the ultrasonic wave. However, the echo signal received by the transducer 44–46 is allowed to reach the RX AMP 60 when the TX/RX switch 72 changes state (from transmit to receive). Generally, the implantable electronic circuit shown in FIG. 5 has the same benefits as described above in connection with the implantable electronic circuit shown in FIG. 4. The RF decode/control section 66 responds to the information received from outside the patient's body that determines which one of the transducers 44–46 is selected at any given time by producing an appropriate MUX control signal that is supplied to the MUX 38 over the MUX control lines 56.

It is also contemplated that the RF decode/control section 66 may cause the MUX 38 to select a different transducer 44–46 for producing/receiving the ultrasonic waves after a predefined number of transmit/receive cycles have elapsed. For example, a different transducer 44–46 may be selected after eight cycles have been implemented to transmit an ultrasonic wave into the stent and to receive back the echoes from the fluid flowing through the stent. By collecting data related to the status of flow through a stent in this manner, it becomes unnecessary to send programming information to the RF decode/control section 66 after each cycle of a transmission of the ultrasonic wave into the fluid in the stent and reception of the echo. Also, by carrying out a predefined number of transmit/receive cycles for the given transducer 44–46 that has been selected by the MUX 38 and averaging the results, a more accurate estimate of fluid velocity through the stent can be obtained than by using only a single transmission and reception of an ultrasonic wave. Since the signal required to instruct the RF decode/control section 66 to change to the next transducer 44–46 is only required after the predefined number of cycles has been completed, the data gathering efficiency of the implantable electronic circuit is improved.

As noted above, the transducers 44–46 shown in FIGS. 1 through 5 need not be ultrasonic transducers; FIG. 6 illustrates an electronic circuit that is particularly applicable for use with transducers 44–46 comprising pressure sensors. Silicon pressure sensors designed to be installed on the radial artery are available from the Advanced Technologies Division of SRI of Palo Alto, Calif. Such pressure sensors could be disposed within the wall of a stent to sense the pressure of fluid flowing through the stent at one or more points. The MUX 38 is used for selecting a specific pressure transducer to provide a data signal that is transmitted to the outside environment via the RF coupling coil 30. In the implantable electronic circuit shown in FIG. 6, a modulator/transmitter (MOD/XMTR) 70 receives the signal from the transducer 44–46 selected by the MUX 38 in response to the MUX selection signal provided over the MUX control lines 56 from the RP decode/control section 66 and, using the signal, modulates a RF signal that is supplied to the RF coupling coil 30. The RF signal transmitted by the RF coupling coil 30 thus conveys the data signal indicating pressure sensed by the selected transducer 44–46. In many cases, it will be preferable to monitor the pressure at the upstream and downstream ends of a stent in order to enable the differential pressure between these ends to be determined. This differential pressure is indicative of the extent to which any blockage in the lumen of the stent is impeding fluid flowing through the lumen. In most cases, parameters such as fluid flow or velocity are better indicators of the status of flow through the stent.

RF Coupling Coil and External Coil Embodiments

FIGS. 7 through 12 illustrate details of several different embodiments for the RF coupling coil 30 that is part of the stent implanted within a patient's body. The RF coupling coil 30 is for receiving RF energy to provide power for the implantable electronic circuits of FIGS. 1 through 6 and for transmitting data relating to the condition of flow and/or other parameter(s) sensed by transducers coupled to one or more stents that have been installed within the patient's vascular system. Optimization of RF coupling between the RF coupling coil 30 on the stent and an external coil is partially dependent upon the propagation characteristics of the human body. Since body tissue is largely water, the relative dielectric constant of mammalian soft tissues is approximately equal to that of water, i.e., about 80. Also, the permeability of body tissue is approximately equal to one, i.e., about that of free space. The velocity of propagation of a RF signal through the body is proportional to the inverse square root of the dielectric constant and is therefore about 11% of the velocity of the signal in free space. This lower velocity reduces the wavelength of the RF signal by an equivalent factor. Accordingly, the wavelength of the RF signal transferred between the implanted RF coupling coil on a stent and the external coil would be a design consideration if the separation distance between the two is approximately equal to or greater than one-quarter wavelength. However, at the frequencies that are of greatest interest in the present invention, one-quarter wavelength of the RF coupling signal should be substantially greater than the separation distance between the RF coupling coil 30 on the stent and the external coil.

One method for optimizing coupling between an implanted coil and a coil that is external to the body is described in *High-Efficiency Coupling-Insensitive Transcutaneous Power And Data Transmission Via An Inductive Link* by C. M. Zierhofer and E. S. Hochmair, IEEE Trans. Biomed. Eng., Vol. 37, No. 7, July 1990, pp. 716–722. This approach allows the frequency of the signal linking the implanted and external coils to vary in response to the degree of coupling between the two coils. Other methods are suitable for coupling signals between the two coils as well.

When the implantable electronic circuit includes the RF coupling coil 30 and a transducer 44–46, but does not include active electronic circuitry, the external system (e.g., external power supply and patient monitoring console 100, FIG. 8, below) senses a parameter related to the electrical input impedance of the external coil. When the external and internal coils are aligned, the inductance and the resistance of the external coil are maximized. The frequency of the signal that is used for adjusting the alignment may be different than the frequency that is used to provide electrical signals to the transducer.

The implantable electronic circuit may include an additional component to facilitate sensing of alignment between the two coils. For example, a metal disc in the implant may be detected and localized by inducing an eddy current in the disc. The external power supply and patient monitoring console may then detect the magnetic field generated by the eddy current in the disc, much as a metal detector operates. Using different frequencies for the location and therapeutic functions may avoid energy losses caused by the eddy currents.

When the implantable electronic circuitry does include active electronic circuitry, a circuit may be included with the therapeutic transducer and RF coupling coil that measures the amplitude of the signal from the external power supply and patient monitoring console that is induced in the RF coupling coil. A signal is transmitted from the implantable electronic circuitry to the external power supply and patient monitoring console, where a display provides an indication of the coupling. The operator may adjust the position of the external coil to optimize coupling between the two coils.

The penetration of RF fields in the human body has been studied extensively in conjunction with magnetic resonance imaging (MRI) systems. RF attenuation increases with frequency, but frequencies as high as 63 MHz are routinely used for whole-body imaging, although some attenuation is observed at the center of the torso at this upper frequency limit. In addition, MRI safety studies have also provided a basis for determining safe operating limits for the RF excitation that define the amplitude of excitation safely applied without harm to the patient.

It is contemplated that for stent implants placed deep within the torso of a patient, RF excitation and frequencies used for communicating data related to the fluid flow through a stent and/or other parameters sensed proximate the stent can be up to about 40 MHz, although higher frequencies up to as much as 100 MHz may be feasible. At 40 MHz, the wavelength of the RF excitation signal in tissue is about 82 cm, which is just that point where wavelength considerations become an important consideration. For shallow implants, RF excitation at a much higher frequency may be feasible. For example, to provide energy to stents that are disposed within a blood vessel only a few millimeters below the epidermis and to receive data from transducers associated with such stents, excitation frequencies in the range of a few hundred MHz may be useful. The dielectric properties of tissue have been studied to at least 10 GHz by R. Pethig, *Dielectric and Electronic Properties of Biological Materials*, Wiley Press, Chichester, 1979 (Chapter 7). Based on this study, no penetration problems are anticipated in the frequency range of interest. The relative dielectric constant of tissue decreases to about 60 at a frequency of 100 MHz and is about 50 at 1 GHz, but this parameter has little effect on power/data signal coupling.

Figure 7:
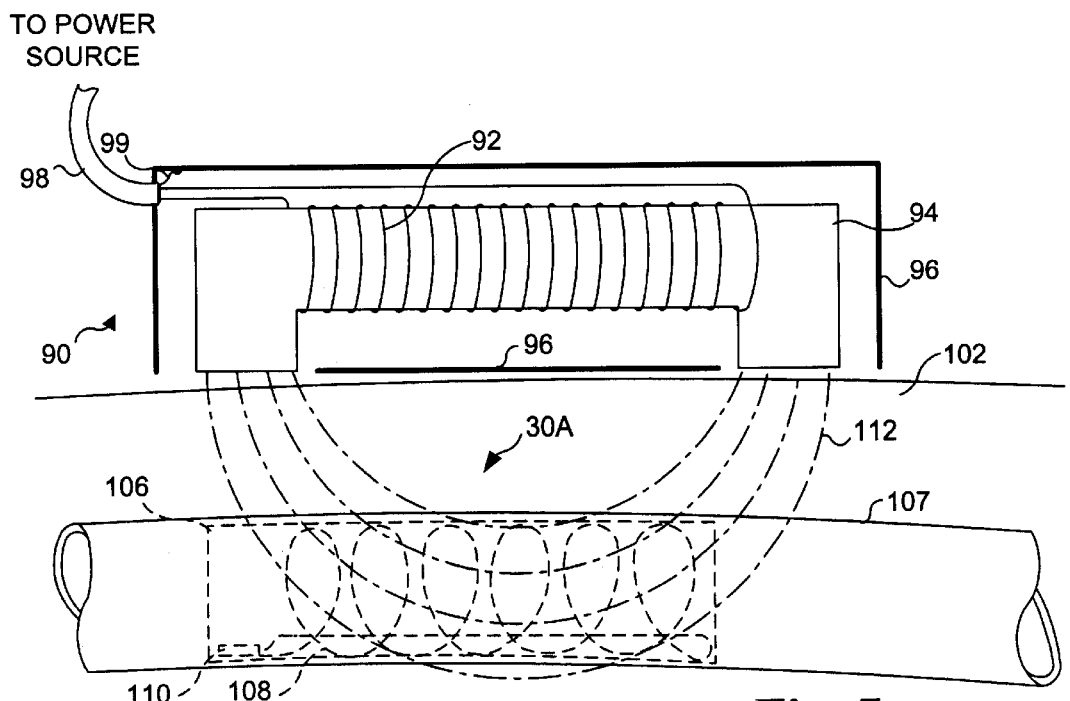
FIG. 7 is a cross-sectional view of a radio frequency (RF) coupling coil in a stent that is implanted in a blood vessel, and an external coil that is electromagnetically coupled to the RF coupling coil.

An external coil 90 and a RF coupling coil 30A shown in FIG. 7 represent one embodiment of each of these components that can be used for coupling electrical energy and conveying data signals across a skin interface 102 or applications in which the RF coupling coil 30A is implanted relatively close to the surface 102 of the skin. For example, the RF coupling coil 30A and the external coil 90 may provide, via magnetic flux lines 112, the coupling required for a system used to monitor a stent implanted in an artery near the skin surface 102. A winding 92 is wrapped around a core 94 forming the external coil 90 and each end of the winding 92 is coupled to a power source through a cable 98.

Although the external coil 90 and the RF coupling coil 30A need not be identical in size, it is generally true that coupling will be optimal if the two devices are of approximately the same dimensions and if the longitudinal axis of the external coil 90 is generally adjacent and parallel to that of the RF coupling coil 30A. By observing the strength of the signal transmitted from the RF coupling coil 30A, it should be possible to position the external coil 90 in proper alignment with the RF coupling coil 30A so that the efficiency of the magnetic coupling between the two is optimized.

To function as the core 94 for the external coil 90, the material used should have a relatively high magnetic permeability, at least greater than one. Although ferrite is commonly used for core materials, sintered powdered iron and other alloys can also be used. Since the magnetic characteristics of such materials are generally conventional, further details of the external coil 90 and the core 94 are not provided.

A housing 96 on the external coil 90 provides RF shielding against electromagnetic interference (EMI). In one embodiment, the housing 96 for the external coil 90 is conductive, grounded and surrounds the external coil 90 except where the surfaces of the generally "C-shaped" core 94 are opposite the RF coupling coil 30A. The RF shield comprising the housing 96 is attached to an internal braided shield 99 of the cable 98. Inside the power supply and patient monitoring console (not shown in FIG. 7) to which the cable 98 is coupled, the shield 99 is connected to ground. The RF shield on the external coil 90, along with shields provided around transducers 44-46 on the stent 106, minimizes external EMI radiation due to the use of the present invention within a patient's body.

For the embodiment shown in FIG. 7, the external coil 90 is magnetically coupled to a spiral winding 108 in the stent 106 that is implanted in a blood vessel 107. The spiral winding 108 comprises the RF coupling coil 30A for the stent 106 and the opposite ends of the spiral winding 108 are coupled to an electronic circuit 110, which may comprise any of the implantable electronic circuits described above in connection with FIGS. 1 through 6. Not shown in FIG. 7 are the one or more transducers 44-46 that are included within the stent 106 to monitor one or more parameters.

The RF coupling coil 30A used in the stent 106 may be either an integral part of the stent 106, or it may instead comprise a separate RF coupling coil 30A that is wound around or through the structure comprising the wall of the stent 106. To function within the body of a patient, the stent 106 must be able to bend and flex with movement of the body, yet must have sufficient surface area and hoop strength to compress the atheriosclerotic material that is inside the blood vessel wall radially outward and to support the vessel wall, maintaining the lumen cross section. Several manufacturers offer stent designs, each fabricated from wire, bent back and forth in a periodically repeating "S" shape or zigzag configuration, forming a generally cylindrical tube. Such stents are considered ideal for use in practicing the present invention, since the wire comprising the wall of the stent 106 can be used for the RF coupling coil 30A. Examples of such stents are the ANGIOSTENT stent made by AngioDynamics, the stent sold by Cordis Corporation, the CARDIOCOIL stent produced by Instent and the WIKTOR stent from Medtronic Corporation.

Figure 8:
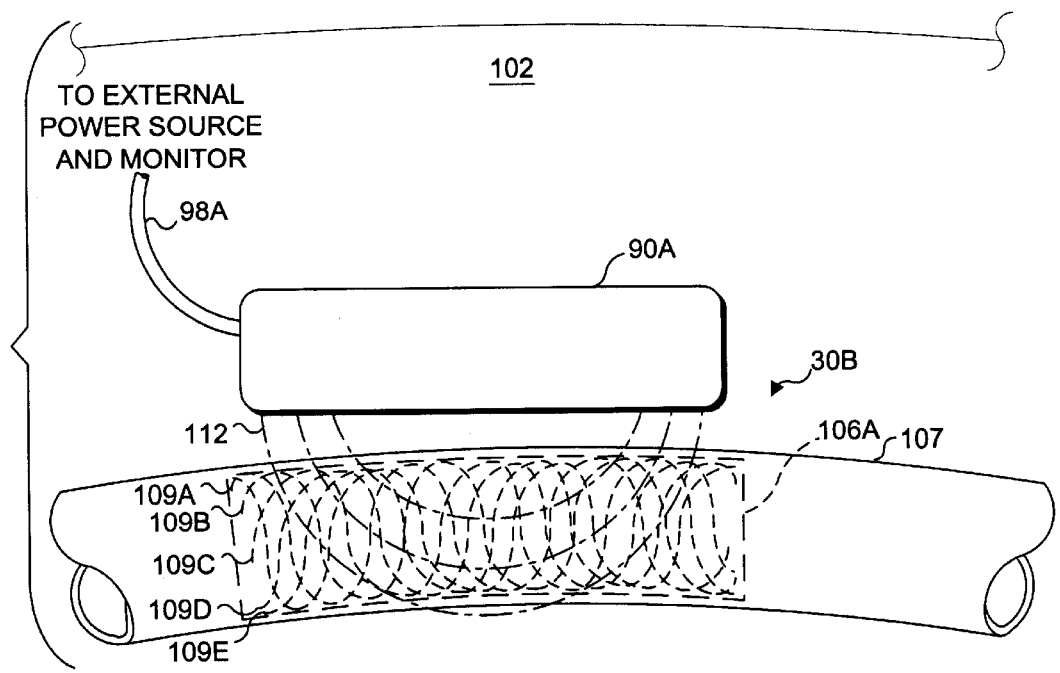
FIG. 8 is a cross-sectional view of a RF coupling coil in a stent implanted in a blood vessel, and includes a block that represents an implanted coil, which is electromagnetically coupled to the RF coupling coil.

FIG. 8 illustrates another embodiment in which an implanted coil 90A disposed outside the blood vessel 107 adjacent to an implanted stent 106A is electromagnetically coupled through magnetic flux lines 112 to the stent 106A using a plurality of electrically isolated and separate helical windings 109A, 109B, 109C, 109D and 109E forming a woven mesh comprising the wall of the stent 106A. Not shown are the implantable electronic circuitry and the transducers 44-46 that are coupled to the windings comprising a RF coupling coil 30B, however, it will be understood that any of the implantable electronic circuits shown in FIGS. 1 through 6, discussed above, can be used for this purpose. However, by using electrically isolated and separate windings 109A–E for the RF coupling coil 30B, it is possible to avoid multiplexing the signals from each different transducer 44-46 used in the stent 106A, since each transducer 44-46 (or sets of transducers 44-46) can transmit data over its own winding and separately receive an excitation signal from the implanted coil 90A. This figure shows the implanted coil 90A coupled to an external power source and monitor through a cable 98A. The cable 98A can either penetrate the dermal layer of the patient's body, passing to the outside environment, or alternatively, may itself be electromagnetically coupled to an external coil, such as the external coil 90 shown in FIG. 7. When the cable 98A from the implanted coil 90A penetrates the dermal layer 102, it is likely that the parameters being sensed by the stent 106A will only need to be monitored for a relatively short time, so that the implanted coil 90A can be removed from the patient's body after the need to monitor the parameters is satisfied. An advantage of the embodiment shown in FIG. 8 is that when the stent 106A is implanted deep within the patient's body, it can be readily energized and the data that it provides can be more efficiently received outside the body by using the implanted coil 90A as an interface, either directly coupled through the skin 102 or magnetically coupled through an external coil.

Stents comprising a woven mesh of fine helical wires are available from certain stent manufacturers. The woven mesh provides the required hoop strength needed to support the wall of a blood vessel after the stent is implanted and expanded or allowed to expand. To maintain the required flexibility for the stent, the wires comprising the woven mesh of such stents are not joined at the intersection points. An example is the WALLSTENT stent, which is sold by Medivent-Schneider. This configuration is also well suited for practicing the present invention. To be used as the RF coupling coil 30B, the wires forming the body or wall of the stent 106A must be electrically insulated from the surrounding tissue of the blood vessel 107 and must be insulated from each other where they cross except at any node wherein the helical turns are linked to form one or more sets of coupled turns. The wire used for this configuration can be either round or flat.

Figure 9:
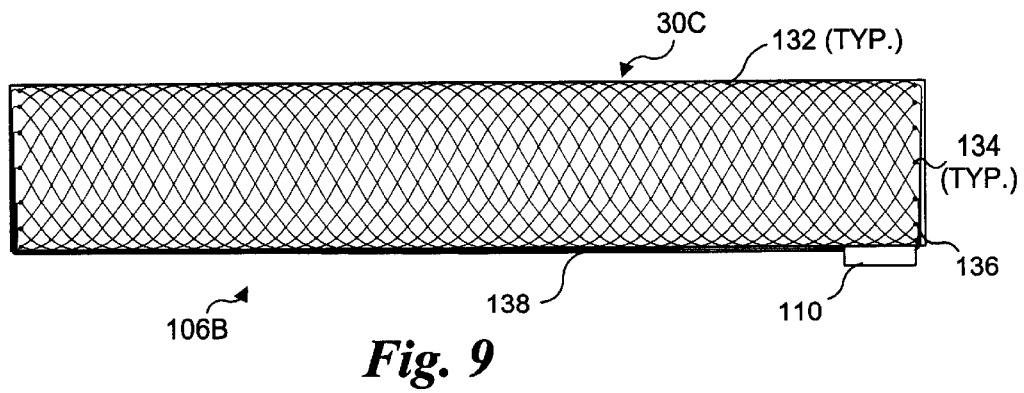
FIG. 9 is a side elevational view of a woven mesh RF coupling coil that comprises a wall of a stent.

An embodiment of a RF coupling coil 30C comprising a stent 106B is shown in FIG. 9 to illustrate the configuration discussed above. The RF coupling coil 30C comprises a woven mesh 132 fabricated from insulated wire so that overlapping segments of the woven mesh 132 do not electrically connect in the center of the stent 106B. At each end of the RF coupling coil 30C, the wires comprising the woven mesh 132 are electrically coupled together at nodes 134, producing the RF coupling coil 30C. The nodes 134 are insulated from contact with body fluids or other conductors.

The couplings at the nodes 134 are preferably not made randomly or in a haphazard fashion between the various wires comprising the woven mesh 132. A first wire comprising a helical coil having, e.g., a first configuration (which may be called a "right hand spiral" or RHS) has a first end coupled to a first end of a second wire comprising a helical coil having a second configuration ("left hand spiral" or LHS; i.e., a mirror image of the right hand spiral). The voltage induced in the two wires is equal, but opposite in sign, and the two wires are thus coupled in series and provide twice the voltage between their second ends than that produced between the first and second ends of either wire alone. Accordingly, the second ends of the first two wires cannot be coupled together at the other end of the woven mesh 132 if these two wires are to contribute to the total electrical energy derived from the woven mesh 132. Rather, the wires must be "daisy chained" in series (i.e., RHS-LHS-RHS-LHS etc.) to provide one embodiment of the RF coupling coil 30C. Alternatively, a first group of wires all having the right hand spiral may all be coupled in parallel (i.e., have the ends at a first end of the woven mesh 132 coupled together, and the ends at a second end of the woven mesh 132 coupled together), with wires having the left hand spiral being similarly treated but in a second group. The groups then may be combined in series or in parallel, or subsets of the wires may be grouped and combined.

When each wire comprising the woven mesh 132 passes around the central axis of the stent 106B through m degrees, and if there are a total of n such wires, then the equivalent number of turns in the RF coupling coil 30C is equal to n×m÷360. Leads 136 and 138 convey signals to and from the nodes 134, coupling the woven mesh 132 to the implantable electronic circuit 110, which may comprise any of the implantable electronic circuits of FIGS. 1 through 6.

The woven mesh structure of the implantable RF coupling coil 30C is often used for stents. However, it should be noted that currently available woven mesh stents are not woven from insulated wire, nor are the nodes of the mesh at each end electrically connected in commercially available stents. In the WALLSTENT stent by Medivent-Schneider, the ends are instead free floating. It is also contemplated that an insulated electrical conductor could be woven into the structure of a commercially available mesh stent. Alternatively, the RF coupling coil 30C could be fabricated from a woven mesh or from a plurality of spiral turns of a conductor and then the mechanical characteristics required of the stent could be achieved by providing an interwoven wire within the RF coupling coil 30C. It is also noted that different implantable electronic circuits can be coupled to separate portions of the woven mesh 132 comprising the RF coupling coil 30C so that the different portions of the RF coupling coil 30C and the implantable electronic circuits are electrically isolated from each other, or as a further alternative, the sections can be coupled in series.

Figure 10:
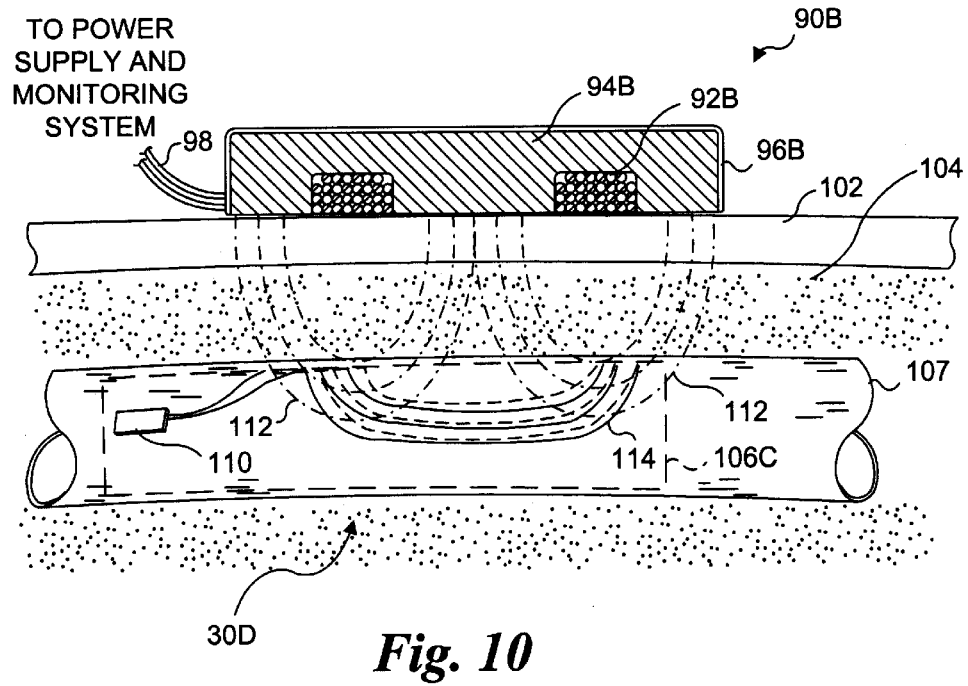
FIG. 10 is a cut-away side elevational view of a further embodiment of an external coil and a side elevational view of a blood vessel in which a stent is implanted that includes a saddle-shaped RF coupling coil integrated within the wall of the stent.

In FIG. 10, a RF coupling coil 30D in a stent 106C is illustrated that comprises a plurality of generally saddle-shaped coils 114 disposed within (or comprising) the wall of the stent 106C. Again, the RF coupling coil 30D is coupled to the implantable electronic circuit 110. Although only a single layer of saddle-shaped coils 114 is illustrated, it is contemplated that a plurality of such interconnected layers could be provided for the stent 106C.

For use in electromagnetically coupling with the RF coupling coil 30D to energize the implantable electronic circuit 110 and to provide signals to and receive data from the transducers 44–46 (not separately shown) on the stent 106C, an external coil 90B is provided that includes a plurality of coils 92B wrapped around a central portion of a generally E-shaped core 94B. Lines of electromagnetic flux 112 are thus produced between the central leg and each of the end legs of the core 94B. It will therefore be apparent that this embodiment of the RF coupling coil 30D and of the external coil 90B achieves optimum coupling when the distance separating the two is minimal. Therefore, the RF coupling coil 30D and the external coil 90B are best used in applications where the stent 106C is disposed relatively close to the dermal layer 102 so that tissue 104 separating the stent 106C from the external coil 90B is only a few centimeters thick. Maximal coupling is achieved when the central axis of the external coil 90B is aligned with the central axis of the coil mounted on the stent 106C.

Figure 11A:
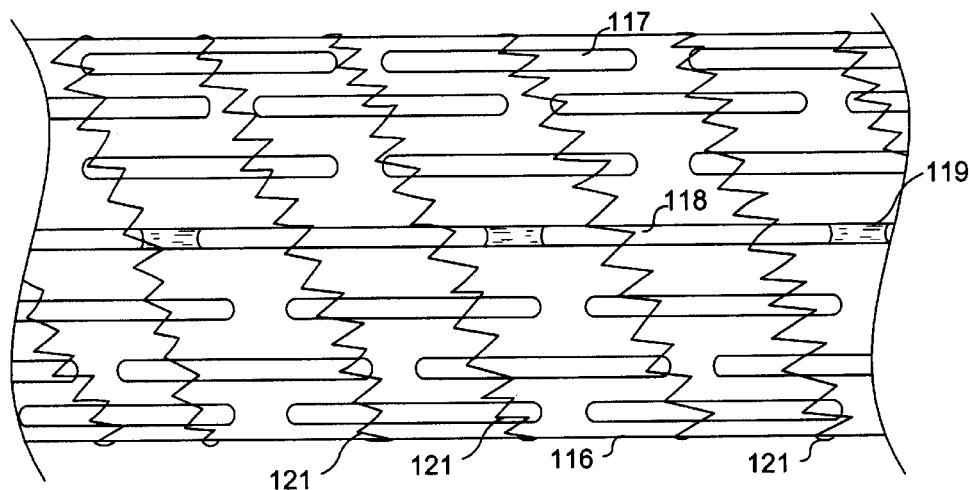
FIG. 11A is a side elevational view (showing only the foreground) of a portion of a metal tube-type stent with nonconductive weld joints, illustrating a RF coupling coil wrapped around the stent in a pre-expansion configuration.

FIG. 11A illustrates an embodiment of a RF coupling coil 121 that is helically coiled around the circumference of a stent fabricated by slotting a metal tube 116. The insulated conductor comprising the RF coupling coil 121 is kinked (or fan-folded) when wound around the metal tube 116 to accommodate expansion of the metal tube 116 once implanted in a blood vessel. The insulation on the RF coupling coil 121 prevents the turns from electrically shorting by contact with the metal tube 116 or with surrounding tissue. Although not shown, the RF coupling coil 121 will likely be adhesively attached to the metal tube 116 at several spaced-apart locations. The ends of the RF coupling coil 121 are coupled to one or more transducers or sensors 44–46 (not shown) through an implantable electronic circuit (also not shown) comprising any of the implantable electronic circuits shown in FIGS. 1 through 6.

The metal tube 116 includes a plurality of generally longitudinally extending slots 117 at spaced-apart locations around the circumference of the stent. These slots 117 provide the expansibility and flexibility required of the stent. This design is similar to the Palmaz-Schatz stent made by Johnson & Johnson Corporation. To avoid providing a shorted turn with the body of the metal tube 116, the generally conventional design of the stent is modified to include a break 118 extending along the entire length of the metal tube 116. The edges of the metal tube 116 are coupled at several joints 119 along the break 118 using a non-conductive material.

Metal-to-ceramic (or metal-to-glass) welded joints 119 are commonly employed in medical implants and other electrical devices. To minimize thermal stress in the joint 119, the metal and the glass or ceramic must have similar thermal expansion coefficients. For example, KOVAR™ alloy, a nickel-iron alloy (29% Ni, 17% Co, 0.3% Mn and the balance Fe) is one material that can be used to form glass to metal seals that can be thermally cycled without damage. This material can be used to form portions of the metal tube 116 disposed along the break 118. Glass or ceramic bonds comprising the joints 119 then will not experience much thermal stress when the temperature of the stent changes. This material is commonly used in lids that are bonded onto ceramic chip carriers in the integrated circuit industry and thus is readily available.

Figure 11B:
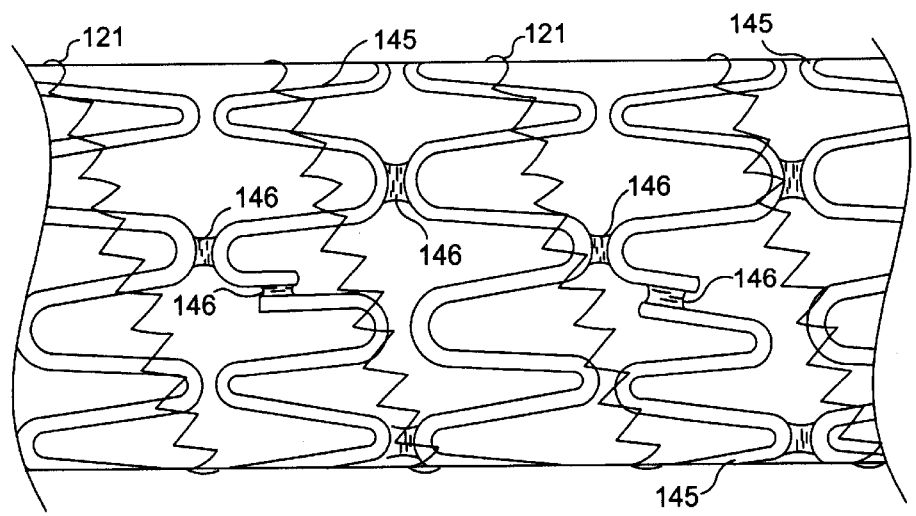
FIG. 11B is a side elevational view (showing only the foreground) of a portion of a zigzag wire stent with nonconductive joints, illustrating a RF coupling coil wrapped around the stent in a pre-expansion configuration.

An alternative design for a stent formed from a non-woven wire 145 about which the RF coupling coil 121 is coiled is illustrated in FIG. 11B. The RF coupling coil 121 is again formed of an insulated conductor that is helically coiled about the circumference of the stent. The body of the stent comprises a plurality of zigzag shapes formed of wire 145 that are joined by non-conductive (i.e., glass or ceramic) joints 146 at spaced-apart points that prevent the wires 145 from forming any shorted turns. This stent configuration is similar to that of the ACS RX MULTI-LINK stent made by Medtronic and the GFX (AVE) stent produced by Arterial Vascular Engineering.

Figure 12:
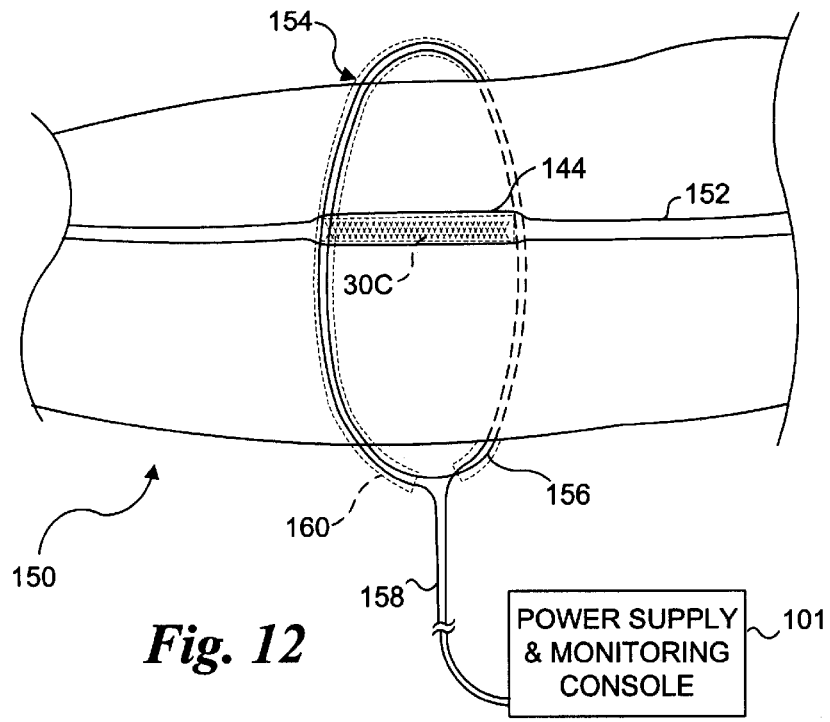
FIG. 12 is a cut-away view of a portion of a limb showing a stent implanted at a substantial depth within a blood vessel, and an external coupling coil that encompasses the stent.

In those cases where stents are implanted relatively deeply inside the patient's body, at some distance from the surface of the patient's skin, an alternative external coil 154 can be employed, generally as shown in FIG. 12. In this example, a stent 144 comprising the RF coupling coil 30C (FIG. 9) is implanted within an artery 152, which is disposed within a thigh 150 of the patient. Alternatively, the stent 144 may be implanted, for example, in the descending aorta, the iliac arteries or to provide therapy to a tumor that is deeply within the abdomen. To couple with the RF coupling coil 30C, the external coil 154 includes a plurality of turns 156 sufficient in diameter to encompass the thigh 150. A RF shield 160 encloses the outer extent of the external coil 154, so the external coil 154 is insensitive to capacitively coupled noise. A lead 158 couples the external coil 154 to a power supply and monitoring console 101. The external coil 154 can be made sufficiently large to encompass the portion of the body in which the implanted stent 144 is disposed such as the torso, a limb of the patient, or the neck of the patient. Coupling is maximized between the external coil 154 and the RF coupling coil 30C (or other RF coupling coil) used on the stent 144 when the central axes of both the RF coupling coil 30C and the external coil 154 are coaxially aligned and when the implanted stent 144 is generally near the center of the external coil 154. Coupling between the RF coupling coil 30C and the external coil 154 decreases with increasing separation and begins to degrade significantly when the implanted stent 144 is more than one external coil 154 radius away from the center point of the external coil 154. In addition, coupling is minimized when the central axis of the external coil 154 is perpendicular to the axis of the RF coupling coil 30C.

Description of the Diagnostic Applications of Transducers

An ultrasonic transducer for monitoring flow or fluid velocity through a stent should be relatively compact and included in or mounted on the wall of a stent. Typical prior art ultrasonic transducers include a planar slab of a piezoelectric material having conductive electrodes disposed on opposite sides thereof. Since such elements are planar, they do not conform to the circular cross-sectional shape of a stent. Moreover, prior art transducers are not compatible for use with a stent that is implanted within a patient's body and which is intended to be left in place for an extended period of time. Also, it is apparent that conventional ultrasonic transducer elements will not readily yield to being deformed into a compact state for implacement within a blood vessel, followed by expansion of a stent body to apply radially outwardly directed force to compress the deposits within a blood vessel.

Figure 13:
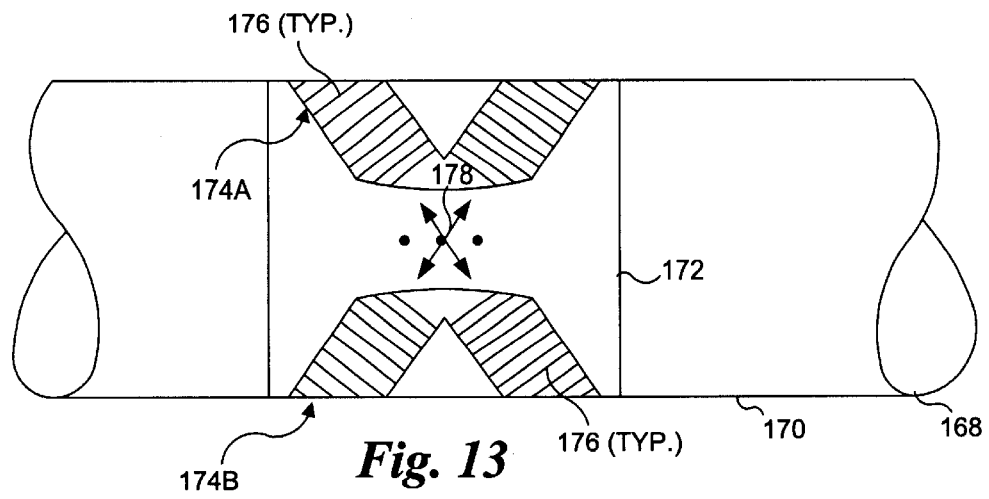
FIG. 13 is a side elevational schematic view of a dual beam conformal array transducer on an expandable carrier band for use in a stent.
Figure 14:
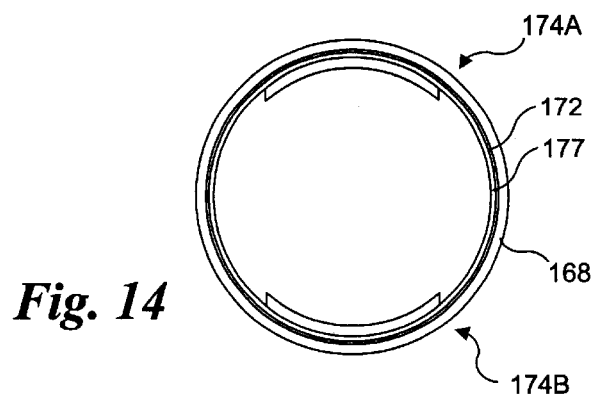
FIG. 14 is an end elevational view of the conformal array transducer of FIG. 13, within a stent.
Figure 15:
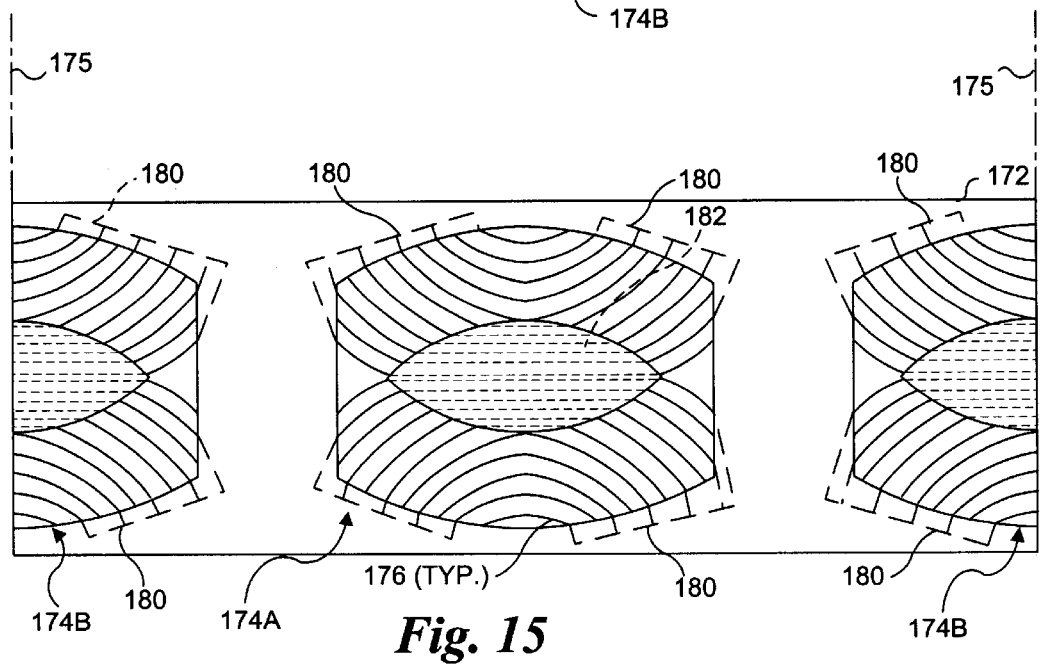
FIG. 15 is a plan view of the conformal array transducer shown in FIGS. 13 and 14, cut along a cut line to display the dual conformal arrays in a flat disposition.

FIGS. 13 through 15 show an embodiment of an extremely low profile ultrasonic transducer comprising conformal transducer arrays 174A and 174B, which are disposed on opposite sides of a stent 168. While the conformal transducer arrays 174A and 174B are described in conjunction with their application as diagnostic transducers, the conformal transducer arrays 174A and 174B are also useful as therapeutic transducers. Since it is contemplated that this type of ultrasonic transducer assembly might be used on several different designs of stents, details of the stent 168 are not illustrated. Instead, only a portion of its outline 170 is shown. Ideally, each conformal transducer array 174A and 174B comprises a piezoelectric plastic used as a transduction material and having sufficient flexibility to allow the transducer elements to conform to the circular cross section of the wall of the stent 168 when the stent 168 is inserted through the patient's vascular system and to flex as the stent 168 is expanded within a blood vessel.

When used for transit time measurements, as shown in FIGS. 13 and 14, the conformal transducer arrays 174A and 174B are disposed generally on opposite sides of the stent 168 and encompass much of the inner circumference of the stent 168. However, when a pulsed Doppler measurement is made using the conformal array transducer 174A, only a single such conformal array transducer 174A is required, since the conformal array transducer 174A first produces an ultrasonic wave that is transmitted into the lumen of the stent 168 and then receives an echo reflected back from the fluid flowing through the stent 168. If used for continuous wave (CW) Doppler measurements, the pair of conformal transducer arrays 174A and 174B disposed on opposite sides of the stent 168 are again needed, one conformal transducer array 174A or 174B serving as a transmitter and the other as a receiver. In each case, it is presumed that the fluid has a non-zero flow velocity component directed along an ultrasonic beam axis of the ultrasonic wave produced by the conformal transducer array 174A or 174B serving as a transmitter.

The conformal transducer arrays 174A and 174B shown in FIGS. 13 through 15 produce ultrasonic beams 178 that are tilted relative to the transverse direction across the stent 168 in substantially equal but opposite angles with respect to the longitudinal axis of the stent 168. Since dual beam transit time measurements are implemented by the conformal transducer arrays 174A and 174B, the results are self-compensating for tilt angle errors. This form of self-compensation is only required where the alignment of the conformal transducer arrays 174A and 174B relative to the longitudinal axis of the stent 168 may be imperfect. For transit time measurements made on stents 168 wherein the alignment of the conformal transducer arrays 174A and 174B relative to the longitudinal axis of the stent 168 remains accurately known, an opposed pair of conformal transducer arrays 174A and 174B disposed on opposite sides of the stent 168 is sufficient so that the added complexity of the dual beam transducer geometry is not required for self compensation.

In the case of pulsed Doppler velocity measurements, a single conformal transducer array 174A would again likely be adequate so long as the alignment of the conformal transducer array 174A to the stent 168 is accurately controlled. If the alignment of the conformal array transducer 174A is not controlled or not well known, a second such conformal transducer array 174B can be used to gather velocity data along a second beam axis using pulsed Doppler velocity measurements. Assuming that the second axis is tilted in an equal but opposite direction as the first axis, the Doppler measurements made by the two conformal transducer arrays 174A and 174B should be self-compensating for tilt errors. In this case, the second conformal transducer array 174B could be mounted on the same or on an opposite side of the stent from that where the first conformal transducer array 174A is mounted to implement the Doppler measurements.

For CW or pseudo-CW Doppler velocity measurements (in which a relatively long duration pulse of ultrasonic waves is produced), the transit signal is applied for a sufficiently long period so that a second conformal transducer array 174B is needed to receive the echo signals. In this case, a single set of diametrically opposed conformal transducer arrays 174A and 174B can be used.

As perhaps best illustrated in FIG. 14, the conformal transducer arrays 174A and 174B need not wrap entirely around the stent 168. In the illustrated embodiment, the conformal transducer arrays 174A and 174B each span an arc of approximately 60° around the longitudinal axis of the stent 168 (i.e., about the center of the circular stent 168 as shown in FIG. 14). This geometry produces a measurement zone through which ultrasonic beams 178 propagate that is nominally equal to about 50% of the outer diameter of the stent 168. If used for Doppler velocity measurements, it is contemplated that the conformal transducer array 174A need cover only a central portion of the stent 168. As a result, the span of the conformal transducer arrays 174A and 174B can be reduced from about 60° to about 45°.

To produce a wide, uniform ultrasonic beam such as that needed for transit time measurements of flow, the conformal transducer arrays 174A and 174B must produce ultrasonic waves having a wave front characterized by a substantially uniform amplitude and phase. As shown in FIG. 13, lateral projections through each of a plurality of transducer elements comprising the conformal transducer arrays 174A and 174B are indicated by straight lines 176. These straight lines 176 indicate the centers of the transducer elements and are perpendicular to the axis of propagation of waves 178 (represented by bi-directional arrows directed along the axes of propagation of the ultrasonic waves). In one embodiment, the spacing between the element centers, i.e., between the straight lines 176, is approximately equal to a phase angle of 90° at the excitation frequency of the conformal transducer arrays 174A and 174B. Thus, starting at the top of FIG. 13 and working downwardly, transducer elements disposed along each of the displayed straight lines 176 produce acoustic waves that are successively delayed by 90°, or one-quarter wavelength in the fluid medium through which the ultrasonic waves propagate. For tissue, a sound velocity of 1,540 meters/second is normally assumed, so that the physical spacing of the projected straight lines would typically be defined by the following:

Projected Spacing in millimeters=$1.54/(4*F_0)$, where $F_0$ is equal to the center frequency in MHz. If zero degrees is assigned to the top-most element of the conformal transducer array 174A, the next element would operate at −90° relative to the top element, followed by an element operating at −180°, and then one operating at −270°, and finally by an element operating at 0° relative to the top electrode. Thus, the conformal transducer array 174A produces a succession of ultrasonic waves spaced apart by a 90° phase shift, thereby achieving a desired phase uniformity across the conformal transducer array 174A.

While the discussion herein is in terms of phase shifts of 90°, it will be appreciated that other types of transducer element spacings or relative displacements may require different phase shifts. For example, three phase transducers are known that employ a phase shift of 120° between adjacent elements. Additionally, physical displacements of the transducer elements in the direction of propagation of the acoustic waves may require different or additional phase shifts between the electrical signals coupled to the elements. It is possible to phase shift these signals to provide a uniform phase front in the propagating acoustic wave using conventional techniques.

Amplitude uniformity can be achieved in the ultrasonic wave front by apodization or "shaving" of the elements of the conformal transducer arrays 174A and 174B. Although shaving could be achieved in a variety of ways, one embodiment controls shaving by varying the area of each element.

In one embodiment, the conformal transducer arrays 174A and 174B are carried on a band 172 made from the piezoelectric plastic material used for the element substrate, which is sized to fit snugly around an outer surface of the stent 168 or inserted into the lumen of the stent 168 (as shown in FIG. 14). The band 172 is intended to position the conformal transducer arrays 174A and 174B in acoustic contact with the wall of stent 168, when the band 172 is wrapped around the stent 168, or to maintain the conformal transducer arrays 174A and 174B against the inner surface of the stent 168, when the band 172 is inserted into the lumen of the stent 168. Contact of the band 172 around the outer surface of the stent 168 assures that the ultrasonic waves produced by the elements of the conformal transducer arrays 174A and 174B are conveyed into the fluid flowing through the interior of the lumen. In one embodiment, the piezoelectric plastic comprising the band 172 is fabricated from a material such as polyvinylidene fluoride (PVDF), poly(vinyl cyanide-vinyl acetate) copolymer (P(VCN/VAc), or poly(vinylidene fluoride-trifluoroethylene) copolymer (P(VDF-TrFE)), available from AMP Sensors of Valley Forge, Pa. In one embodiment, P(VDF-TrFE) is used because of its high piezoelectric coupling and relatively low losses.

Referring now to FIG. 15, further details of the conformal transducer arrays 174A and 174B are illustrated. In this embodiment, adjacent elements of the conformal transducer arrays 174A and 174B produce ultrasonic waves differing by 90°. In the view shown in FIG. 15, a cut line 175 intersects the lateral center of the conformal transducer array 174B. In practice, any cut would more likely extend through the band 172 at a point approximately midway between the conformal transducer array 174A and the conformal transducer array 174B. Electrodes comprising each element of the conformal transducer arrays 174A and 174B can be photolithographically generated on the piezoelectric plastic substrate comprising the band 172. Alternatively, the elements can be formed on a non-piezoelectric material comprising the band 172, and then the material with the elements formed thereon can be bonded to a piezoelectric substrate in each area where a conformal array transducer element is disposed. In this latter embodiment, it is contemplated that a flexible circuit material such as a polyimide could be employed for the band 172 and that conventional photolithographic processing methods might be used to fabricate the conformal array transducer circuitry on the band 172. Further, the centers of alternating conformal array elements are coupled together electrically via conductors 180 (shown as dashed lines) in FIG. 15. Not shown in FIGS. 13 through 15 are the leads that extend from an implantable electronic circuit used to drive the conformal transducer arrays 174A and 174B. Any of the implantable electronic circuits shown in FIGS. 1 through 6 could be used for the implantable electronic circuits.

The pattern of elements comprising each of the conformal transducer arrays 174A and 174B and the boundary of each conformal transducer array 174A and 174B (top and bottom as shown in FIG. 15), define sinusoidal segments. The period of the sine wave from which these sinusoidal segments are derived is approximately equal to the circumference of the band 172. Further, the amplitude of that sine wave generally depends on the desired beam angle relative to the longitudinal axis of the stent. For the sinusoidal segment employed for each electrode, the amplitude is defined by:

Amplitude=$D*\tan\Theta$.

Similarly, the amplitude of the sinusoidal segment defining the boundary of each conformal array 174A and 174B is defined by:

Amplitude=$D/(\tan\Theta)$, where $\Theta$ is equal to the angle between the longitudinal axis of the stent 168 (see FIG. 13) and the ultrasound beam axis 178 and D is equal to the external diameter of the stent 168. Accordingly, it should be apparent that one sinusoidal template could be used to draw all of the transducer elements and a second sinusoidal template (differing only in amplitude from the first) could be used to draw the boundary of each conformal array transducer 174A and 174B. The transducer elements are displaced or spaced apart from one another as required to achieve the phase relationship described above in connection with FIG. 13. In addition, the actual physical electrode pattern and placement of the elements on the band 172 can be determined by finding intersection loci between the band 172 as wrapped around (or within the inner circumference of) the stent 168 and equally-spaced planes. The spacing between these planes is defined by the equation noted above for the projected spacing.

The conductors 180 that couple to adjacent transducer elements differ in phase by 90°. There are two ways to achieve the 90° phase variation between the ultrasonic waves produced by successive electrodes in the conformal transducer arrays 174A and 174B. In the first approach, a uniformly polarized piezoelectric plastic substrate is used and every fourth element is coupled together, producing four groups of elements or electrodes that produce ultrasonic waves having phase relationships of 0°, 90°, 180° and 270°, respectively. Alternatively, a zone polarized piezoelectric plastic substrate could be used and every other element can be coupled together (as shown in FIG. 15). Each of these two groups is then coupled to provide an in phase and a quadrature phase transceiving system, so that ultrasonic waves are produced by adjacent elements in each group have a relative phase relationship of 0° and 90°. In the first approach, a multi-layer interconnect pattern is required to couple to all traces for each of the transducer elements in the four groups. In addition, a more complex four-phase electronic driving system that includes a phase shifter is required. Specifically, the signal applied to each of the four groups must differ by 90° between successive elements to achieve the 0°, 90°, 180° and 270° driving signals. The phase shifter, e.g., may be included in the modulator that drives the conformal transducer arrays 174A and 174B (which may be included as a part of the RF decode section 40 of FIGS. 1 through 3 or the RF decode/control section 66 of FIGS. 4 through 6), and provides the phase shifted excitation signals applied to each successive element of the conformal transducer arrays 174A and 174B.

In the second approach, which may be preferred in some embodiments because it may simplify the electronic package required and because it may facilitate use of a simpler, double-sided electrode pattern, the piezoelectric plastic material must be locally poled in a specific direction, depending upon the desired phase of the electrode at that location. A poling direction reversal provides a 180° phase shift, eliminating the need for 180° and 270° phase-shifted signals. Thus, the zones of the substrate designated as 0° and 90° would be connected to the in-phase and quadrature signal sources with the elements poled in one direction, while zones for elements designated to provide a relative phase shift of 180° and 270° would be connected to the in-phase and quadrature signal sources with the elements poled in the opposite direction. The elements producing ultrasonic waves with a relative phase relationship of 0° and 180° would comprise one group (e.g., in-phase) and the elements producing ultrasonic waves with a relative phase relationship of 90° and 270° would comprise a second group (e.g., quadrature). Poling the different groups of elements in local regions in opposite directions is achieved by heating the material above the Curie temperature, applying electric fields of the desired polarities to each of those areas and then cooling the material below the Curie temperature while maintaining the electric fields. This occurs during manufacture of the conformal transducer arrays 174A and 174B. The final element wiring pattern required to actually energize the conformal transducer arrays 174A and 174B when they are employed for monitoring flow and/or velocity of fluid through the vessel 170 would preclude applying electric fields in opposite polarity. Accordingly, the required poling relationship would have to be performed using either temporary electrodes or by providing temporary breaks in the actual electrode pattern employed in the final conformal transducer arrays 174A and 174B.

In one embodiment, to achieve a desired frequency of operation, it is contemplated that the electrode mass would be increased to a point well beyond that required for making electrical connections. This added mass would act together with the piezoelectric plastic material to form a physically resonant system at a desired frequency. In this manner, a relatively thinner and more flexible piezoelectric plastic material can be used for the substrate comprising the band 172. Use of mass loading is conventional in the art of ultrasonic transducer design.

While the fluids within the vessel 170 may provide an effective ground plane, in one embodiment, a conductive layer 177 (see FIG. 14) is included. The conductive layer 177 may be disposed on the inside of the band 172 as illustrated (between the conformal array transducer 174A and the band 172). In one embodiment, the conformal array transducer 174A comprises a sandwich of two layers of piezoelectric plastic, with the driven electrodes disposed between the two layers of piezoelectric plastic, and ground planes disposed to either outside surface of the conformal array transducer 174A. The transducer then comprises a ground plane, a layer of piezoelectric plastic, a layer of driven electrodes, a layer of piezoelectric plastic and the other ground plane. This embodiment has the advantage that the conformal array transducer 174A is well shielded and further is electrically isolated from body fluids. Other arrangements will also be apparent to those of skill in the art. When the conformal transducer arrays 174A and 174B are used to transmit ultrasonic waves, the conductive layer 177 may be floating (a "virtual ground") or may be coupled to a ground or common circuit (e.g., 34, FIGS. 1 through 6). When the conformal transducer arrays 174A and 174B are used to receive ultrasonic waves, the conductive layer 177 should be coupled to a common circuit or ground to reduce noise and EMI.

Figure 16A:
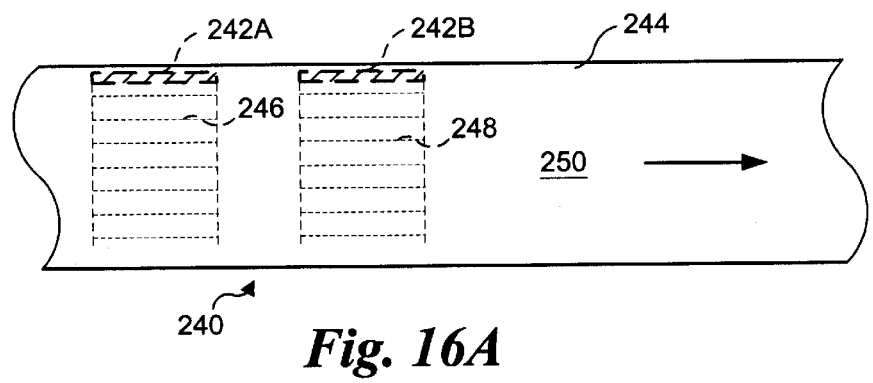
FIG. 16A is a cross-sectional side view of a portion of a stent in which are disposed transversely oriented transducers for monitoring flow using correlation measurements.
Figure 16B:
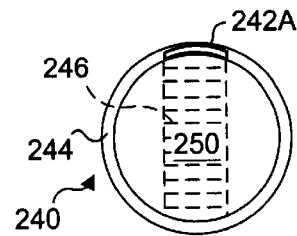
FIG. 16B is a transverse cross-sectional view of the stent and transversely oriented transducers shown in FIG. 16A.

In FIGS. 16A and 16B, an alternative approach for monitoring the velocity of a fluid through an interior 250 of a stent 240 is illustrated. A pair of ultrasonic transducers 242A and 242B may be realized as conformal transducer arrays, e.g., as described in conjunction with FIGS. 13 through 15, or may be realized in other forms, and may find application as therapeutic transducers in addition to being useful as diagnostic transducers.

In the embodiment illustrated in FIGS. 16A and 16B, the pair of ultrasonic transducers 242A and 242B are mounted in relatively close proximity within a wall 244 of the stent 240. Alternatively, the ultrasonic transducers 242A and 242B may be disposed externally in contact with the outer surface of a stent (not shown). The ultrasonic transducers 242A and 242B each produce a pulse and receive an echo back from fluid flowing through the interior 250 of the stent 240, the echoes being scattered from the fluid flowing therein. In this embodiment, the signal received from the ultrasonic transducer 242A in response to the echo is correlated with a similar signal from the ultrasonic transducer 242B, resulting in a time delay estimate. The velocity of the fluid is then computed by dividing a distance between the center of the ultrasonic transducer 242A and the center of the ultrasonic transducer 242B by the time delay that was determined from the correlation analysis. This is explained in more detail as follows.

The interaction of the blood with the ultrasound, even when it is moving at constant velocity, gives rise to a moving acoustic "speckle" pattern. The term speckle, as used herein, has a similar meaning in ultrasonics as in optics. It results any time that narrow band illumination is used. Optical speckle is visible when a laser (e.g., a pointer) illuminates a plain white wall. When illuminated with wideband illumination, the wall appears white and smooth. When illuminated with laser light, the wall appears to have bright and dark spots, hence the term speckle. Acoustic speckle is visible in medical ultrasound images, when the system is used to image homogeneous soft tissues such as the liver. As in optics, the acoustic speckle pattern is stationary and constant unless the tisse or flood is moving with respect to the imaging system. The same phenomenon is exploited in Doppler systems. When the echo return from moving blood is constant, there is no observable Doppler shift in the echo signal.

The blood consists of thousands of scatterers, and the ultrasound reflects from ensembles of these scatterers. The amplitude and phase of the echo, at a given range, depends on the local distribution of scatterers, which is random. The random signal of echo amplitude and phase at a given depth repeats as the blood flows past the second ultrasonic transducer 242B, if the spacing between the two ultrasonic transducers 242A and 242B is such that the ensembles of scatterers have not changed significantly, i.e., if the two ultrasonic transducers 242A and 242B are close enough to each other that turbulence has not significantly disrupted the ensembles of scatterers. Correlation of nominally identical random patterns that are displaced in time by an amount equal to the time required for the blood to move from the first beam to the second one allows the velocity to be determined when the separation between the two ultrasonic transducers 242A and 242B is known.

In other words, the first ultrasonic transducer 242A receives an echo signal that provides a speckle "image"—where the distance from the ultrasonic transducer 242A is along the vertical dimension in FIGS. 16A and 16B, and the successive echo returns are along the horizontal dimension. The two "images" from the two ultrasonic transducers 242A and 242B are correlated in the horizontal dimension, and what results is an instantaneous map of travel time vs. depth.

The sampling aperture for this system is much shorter than the time required for a heartbeat. Accordingly, a series of measurements, which may be taken during the interval between two successive heartbeats, may be processed or compared to determine peak, minimum and average blood velocity when these data are desired.

Unlike a Doppler system, the echoes in a correlation type transducer system like that shown in FIGS. 16A and 16B are not frequency shifted. Instead, the velocity signal is extracted by correlating the echo amplitude versus time signals for a pair of range bins. The velocity versus time is independently determined for each range bin, resulting in a time dependent velocity profile across the diameter of the stent 240.

Figure 17:
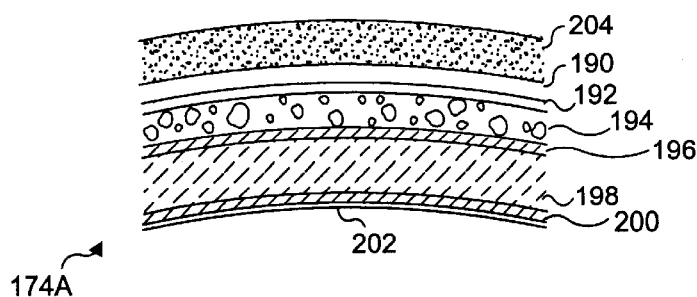
FIG. 17 is an enlarged partial transverse cross-sectional view of the layers comprising the conformal array transducer disposed on a stent within a blood vessel.

The conformal transducer arrays 174A and 174B of FIGS. 13 through 15 can be formed on the band 172, but alternatively, can be included within the structure of a stent, i.e., within its wall. FIG. 17 illustrates a portion of a cross-sectional view of the conformal array transducer 174A of FIGS. 13 through 15 fabricated in a stent wall 190. The entire conformal array transducer 174A is fitted within the stent wall 190. Details of the stent wall 190 are not illustrated, since it is contemplated that many different types of stent configurations are suitable for carrying the conformal transducer arrays 174A and 174B. The stent wall 190 is shown inside a blood vessel wall 204. A biocompatible outer coating 192 comprises the next layer, protecting the conformal transducer arrays 174A and 174B from contact with bodily fluids. In one embodiment, the outer coating 192 comprises PARYLENE™ material, available from Specialty Coating Systems of Indianapolis, Ind. Outer coatings 192 comprising PARYLENE™ material may be grown to a desired thickness via vapor coating. In one embodiment, the outer coating 192 is grown to a thickness of between 0.0001" to 0.0002" (2.5 to 5 microns). Below the outer coating 192 is an acoustic backing 194 comprising a conventional, or a syntactic foam, ie., a polymer loaded with hollow microspheres, that serves both for acoustic isolation and dampening and to minimize capacitive loading.

In one embodiment, the acoustic backing 194 comprises one volume of EPOTEK 377 or 301-2 epoxy glue available from Epoxy Technology of Billerica, Mass. mixed, e.g., with two or more volumes of microballoons available from PQ Corp. of Parsippany, N.J. Microbubbles such as PM6545 acrylic balloons having an average diameter of 100 microns are employed in one embodiment, with the acoustic backing being 10 to microballoons thick (one to two mm). The acoustic backing 194 has a relatively low dielectric constant (e.g., <10), thereby minimizing capacitive loading between the electrodes and surrounding tissue. The acoustic backing 194 thus insulates the transducer elements from the surrounding fluid and tissue in a capacitive sense and also in an acoustic sense. The next layer comprises a rear electrode 196. A front electrode 200 is spaced apart from the rear electrode by a piezoelectric plastic layer 198. In one embodiment, the front electrode 200 is also the conductive layer 177 of FIG. 14. As noted above, in the embodiment illustrated in FIGS. 13 through 15, the piezoelectric plastic layer 198 of FIG. 17 comprises the band 172 of FIGS. 13 through 15. The piezoelectric layer 198 (or the band 172) has a relatively low dielectric constant, e.g., from about six to eight, compared to tissue (approximately 80).

In one embodiment, the rear electrode 196 and the front electrode 200 comprise multi-layer structures (although separate layers are not shown). For example, the electrodes 196 and 200 will include a metallic layer that bonds well to the piezoelectric plastic layer 198, for example, titanium, followed by a highly conductive layer, for example, copper, followed by an oxidation resistant layer, for example, gold, and includes other metallic barrier layers, where appropriate, to prevent reaction between these layers. Such multi-layer systems are conventional and are suited for use as the electrodes 196 and 200 in the conformal transducer arrays 174A and 174B.

In one embodiment, the front electrode 200 is the "common electrode" for the transducer elements and serves as a RF shield. A front coating 202 serves as an acoustic coupling between the conformal transducer arrays 174A and 174B and the fluid in the lumen of the stent. In addition, the front coating layer 202 serves as a biocompatible layer, providing a barrier to fluid ingress into the conformal array transducers 174A and 174B.

In both the conformal array transducers 174A and 174B provided in the band 172 (as shown in FIGS. 13 through 15) and the conformal array transducer 174A included within the structure of the stent wall 190, as illustrated in FIG. 17, it is contemplated that adhesive layers (not shown) may be used between the various layers. However, certain layers such as the front and rear electrodes 200 and 196 will likely need not be adhesively coupled to the piezoelectric layer 198 if photolithographically formed on the piezoelectric layer 198. Other layers may not require an adhesive to couple to adjacent layers, e.g., if formed of a thermoset material that self bonds to an adjacent layer when set.

Figure 18:
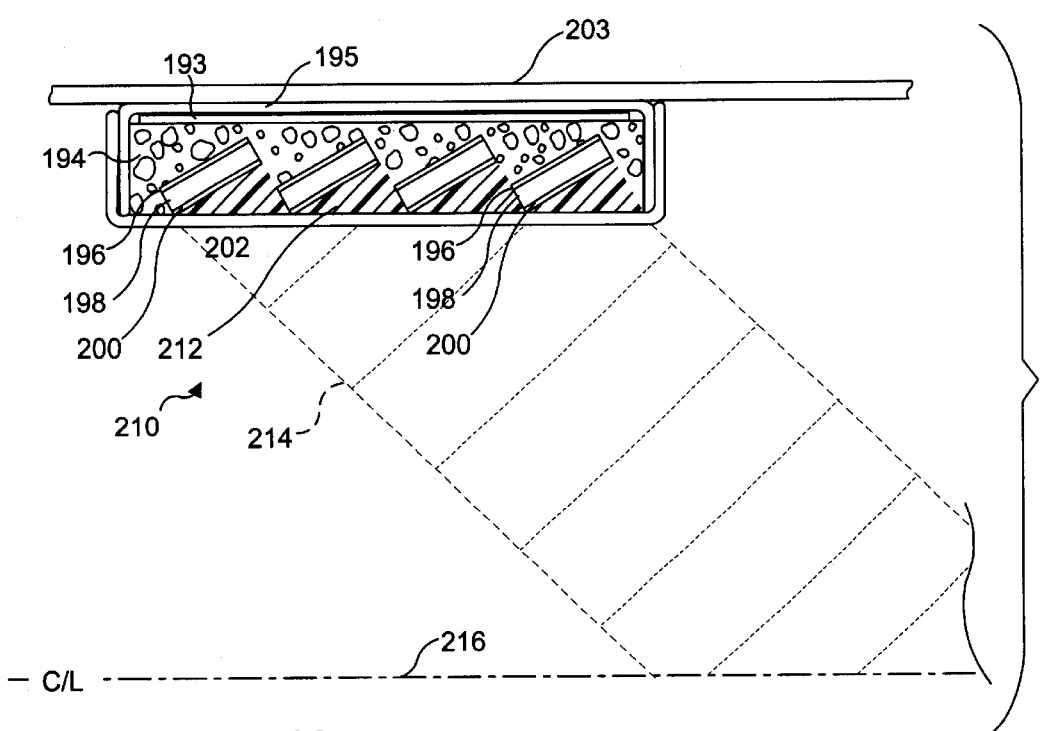
FIG. 18 is an enlarged partial cross-sectional side view of a tilted-element transducer array disposed within a stent.

As noted above, one of the advantages of the conformal transducer arrays 174A and 174B is a relatively low profile. In some cases, a stent may integrally accommodate a relatively thicker profile transducer assembly. An embodiment of a tilted element transducer 210 coupled to a stent 203 that is useful as a diagnostic transducer or as a therapeutic transducer is illustrated in FIG. 18. Each element comprising the tilted element transducer 210 includes the rear electrode 196 and the front electrode 200 disposed on opposite sides of the piezoelectric material 198. Conventional prior art transducers for producing an ultrasonic waves use a single such element that has a substantially greater width that is often too great for inclusion within a stent assembly. In contrast, the tilted element transducer 210 includes a plurality of elements like those shown in FIG. 18 that minimize the radial height (or thickness) of the tilted element transducer 210.

An outer coating 195 again serves the function of providing a biocompatible layer to protect the transducer components contained therein from exposure to bodily fluids. When the outer coating 195 comprises PARYLENE alone, an RF shield 193 extends over the tilted elements, immediately inside the outer coating 195. When the outer coating 195 comprises a container (as illustrated), it includes an outer coating of a material such as PARYLENE. When the outer coating 195 comprises a conductive material, a separate RF shield such as the RF shield 193 may not be required. The acoustic backing 194 is disposed below the RF shield 193 or the outer coating 195.

An acoustic filler material 212 is disposed between the front electrode 200 and the front coating 202, on the interior surface of the stent 203, and is used to fill in the cavities in front of the transducer elements. The acoustic filler material 212 is characterized by a relatively low ultrasonic attenuation, so that it readily conveys the ultrasonic waves produced by the transducer elements into the lumen of the stent 203. In one embodiment, in order to minimize reverberations of the ultrasonic waves in this acoustic filler material 212, its acoustic impedance, which is related to sound velocity times density, is approximately equal to that of the fluid in the vessel. The velocity of sound in the acoustic filler material 212 should also be close to that of the fluid flowing through the stent 203 so that the sound beam is not significantly deflected by the acoustic filler material 212. In another embodiment, the acoustic filler material 212 has a relatively low sound velocity compared to the fluid. In this embodiment, the acoustic filler material 212 acts as an acoustic lens that deflects the sound being produced by the elements of the tilted element transducer 210. For example, materials such as silicones or fluorosilicones typically having sound velocities about 1000 meters per second (compared to a sound velocity of approximately 1540 meters per second for blood) may be used. Low velocity lenses are conventional. A benefit of using a low velocity acoustic filler material 212 is that the elements of the tilted element transducer 210 can be tilted about 30% less than would be required otherwise. As a result, the overall height of the tilted element transducer 210 portion of the stent 203 can be made about 30% thinner than would be possible without the low velocity acoustic filler material 212. In combination, the plurality of tilted elements of the tilted element transducer 210 produce an ultrasonic wave 214 that propagates at an angle relative to the longitudinal axis of the stent, which is represented by a center line 216 in FIG. 18.

Figure 19A:
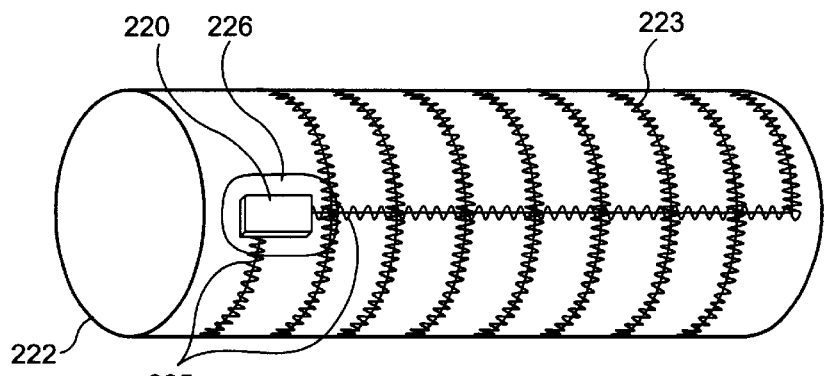
FIG. 19A is an isometric view of an integrated circuit (IC) transducer mounted on a tubular stent.

FIG. 19A is an isometric view of an implantable integrated circuit (IC) transducer 220 mounted on a tubular stent 222, which may comprise a stent similar to that described in conjunction with FIG. 11A above. Wires form a RF coupling coil 223 coupled to the implantable IC sensor 220 via wires 225. The wires comprising the RF coupling coil 223 are formed in a zigzag shape to allow for expansion of the tubular stent 222 when it is installed. The implantable IC sensor 220 may include diagnostic or therapeutic transducers. In one embodiment, the sensing apparatus of the implantable IC sensor 220 faces the interior of the tubular stent 222, as is described more fully with respect to FIG. 19B below.

Figure 19C:
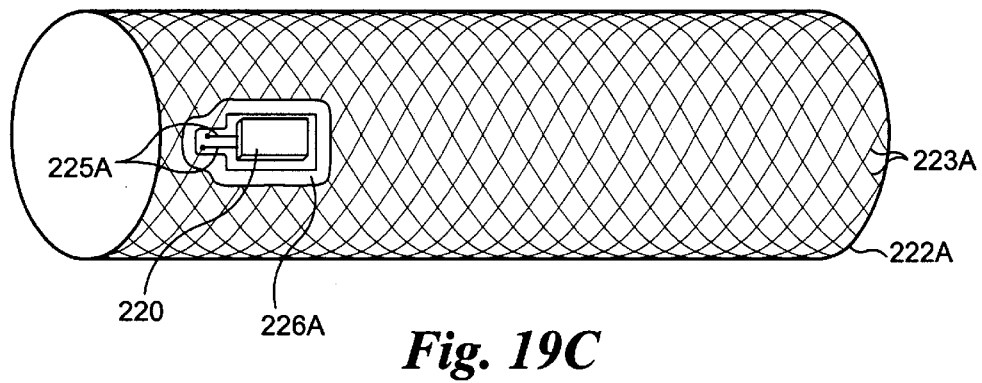
FIG. 19C is an isometric view of the implantable IC transducer mounted on a woven mesh stent.
Figure 19D:
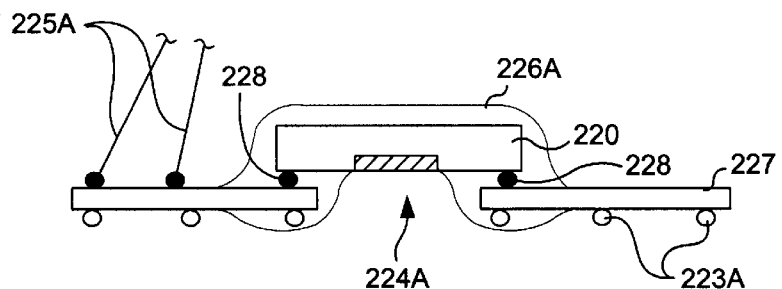
FIG. 19D is an enlarged partial cross-sectional side view of the implantable IC transducer mounted on the woven mesh stent.
Figure 19B:
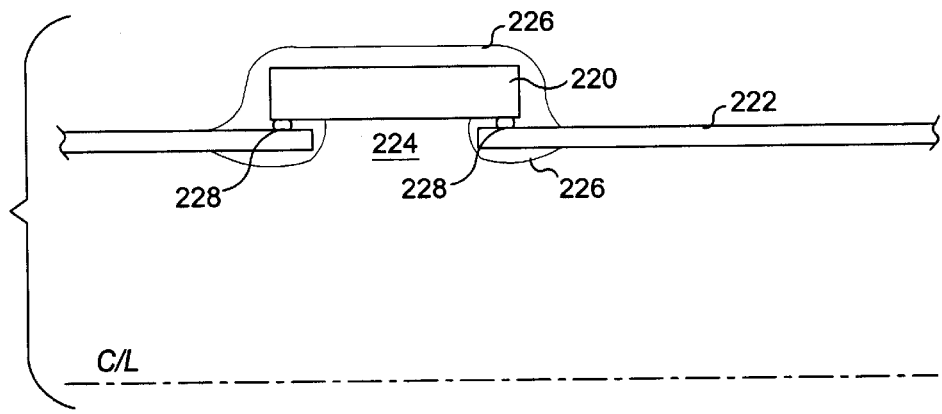
FIG. 19B is an enlarged partial cross-sectional side view of the implantable IC transducer mounted on the tubular stent.

FIG. 19B illustrates the implantable IC sensor 220 mounted on the tubular stent 222, so that the implantable IC sensor 220 overlies a sensor window opening 224 in the tubular stent 222. Conductive adhesive or solder 228 couples the implantable IC sensor 220 contacts to the tubular stent 222 (or to conductors that are coupled to one of the implantable electronic circuits shown in FIGS. 1 through 6). A biocompatible coating 226 (analogous to the biocompatible coating 192 of FIG. 17) encloses the implantable IC sensor 220, except in the area of the sensor window opening 224 through which the implantable IC sensor 220 is in contact with the fluid flowing through the lumen of the tubular stent 222. The portion of the tubular stent 222 on which the implantable IC transducer 220 is mounted may be made rigid, e.g., by thickening it, to prevent damage to the implantable IC transducer 220 during the installation of the tubular stent 222. Optionally, a circuit board (not illustrated in FIG. 19B) may be included between the implantable IC transducer 220 and the tubular stent 222 to facilitate making electrical interconnections to the RF coupling coil 223.

FIG. 19C illustrates an embodiment wherein the implantable IC transducer 220 is coupled to a woven mesh stent 222A. The woven mesh stent 222A comprises wires woven to form a mesh comprising a RF coupling coil 223A as described in conjunction with FIGS. 8 and 9 above. Wires 225A couple the RF coupling coil 223A to the implantable IC transducer 220. The implantable IC sensor 220 may include diagnostic transducers, and the woven mesh stent 222A may include therapeutic transducers (not illustrated). In one embodiment, the sensing apparatus of the implantable IC transducer 220 is held in place via an encapsulant 226A to face the interior of the woven mesh stent 222A, as is described more fully with respect to FIG. 19D below.

FIG. 19D is an enlarged partial cross-sectional side view of the implantable IC transducer 220 mounted on the woven mesh stent 222A of FIG. 19C. The implantable IC transducer 220 is coupled to the wires comprising the body of the woven mesh stent 222A by the encapsulant 226A which may also serve as a biocompatible fluid barrier and as an insulator. This keeps the implantable IC transducer 220 from contacting body fluids except at the sensing interface which is mounted within an opening 224A in the wall of the woven mesh stent 222A. A flexible circuit substrate 227 optionally is employed to provide mechanical attachment and electrical coupling to the implantable IC transducer 220 via solder bumps 228 or other conductive and mechanically robust interconnection. In the embodiments of FIGS. 19A through 19D, the implantable IC transducer 220 may comprise the implantable electronic circuits of any of FIGS. 1 through 6 and the stents 222 and 222A may also include other transducers such as diagnostic or therapeutic transducers.

It is contemplated that the implantable IC transducer 220 might be used for measuring parameters such as pressure, temperature, blood gas concentration and insulin level or the levels of other metabolite such as glucose or sodium in the blood stream of a patient in which a stent that includes the IC sensor 220 is implanted. As explained above, the implantable IC sensor 220 is electrically energized with electrical power that is electromagnetically coupled to the RF coupling coil 223A that comprises the stent body 222A or which is incorporated as one or more separate insulated windings within the stent wall structure. Signals produced by the IC sensor 220 are converted to data signals, which are electromagnetically coupled to a monitor outside the patient's body, also as explained above. In certain applications of implantable IC sensors 220, it may be advantageous to perform a differential measurement between two spaced-apart locations on the stent body 222 or 222A. Thus, to monitor fluid flow through the lumen of a stent 222 or 222A, a differential pressure measurement made by transducers respectively disposed adjacent the proximal and distal ends of the stent 222 or 222A provide an indication of blood flow and of any blockage with the lumen of the stent 222 or 222A.

If an external source of heat is applied to heat the blood or other fluid flowing through the lumen of a stent 222 or 222A, flow can be determined by monitoring the temperature of the fluid with IC sensors 220 that are responsive to that parameter. An external source of RF energy electromagnetically coupled into the stent 222 or 222A, as disclosed above, can both provide the electrical power for the components of the stent transducer system and provide the power for heating the fluid. To avoid tissue damage, the maximum stent temperature should remain below 42.5° C., which is well established as the temperature above which hyperthermia and irreversible tissue damage occur. By analyzing the resultant temperature vs. time "thermal washout" curve, the flow rate of fluid through the stent 222 or 222A can be determined. A differential temperature measurement made by temperature sensors disposed adjacent the opposite ends of the stent 222 or 222A could also be used to determine flow through the stent lumen. Using the signals from these sensors, two temperature vs. time curves can be developed simultaneously. Differences in the observed thermal washout curves should be primarily a function of flow through the lumen and thus indicative of that parameter.

Other methods can be employed to determine flow based on temperature measurements. For example, by modulating the RF power used to heat the stent 222 or 222A, the temperature vs. time curves will exhibit the modulation frequency. The temperature vs. time curves produced by spaced-apart temperature sensors can be filtered with a relatively narrow bandwidth filter. The phases of the two filtered signals are compared to extract a flow velocity through the stent 222 or 222A. The signal processing concept of this approach is conceptually similar to that used for measuring cardiac output using a catheter-mounted heater and temperature sensors, as disclosed in U.S. Pat. No. 5,277,191 entitled Heated Catheter For Monitoring Cardiac Output.

Several types of IC sensors 220 that might be incorporated within a stent in accord with the present invention are disclosed in previously issued U.S. patents. For example, U.S. Pat. No. 4,020,830 (and re-examination certificate B1 4,020,830) entitled Selective Chemical Sensitive FET Transducers and U.S. Pat. No. 4,218,298 entitled Selective Chemical Sensitive FET Transducer describe chemical field effect transistor (FET) transducers that are sensitive to specific chemical substances or to their properties. U.S. Pat. No. 4,935,345 entitled Implantable Microelectronic Biochemical Sensor Incorporating Thin Film Thermopile discloses an implantable microelectronic biochemical sensor that incorporates a thin film thermopile for use in monitoring concentrations of glucose or other chemicals present in the blood stream. Various types of pressure sensing devices appropriate for incorporation in the wall of a graft are readily available from a number of different commercial sources, including SRI Center for Medical Technology of Palo Alto, Calif.

Other prior art devices are potential candidates for use as IC sensors 220 on stents 222 or 222A. In Evaluation of a Novel Point-of-Care System, the I-Stat Portable Clinical Analyzer, CLINICAL CHEMISTRY, Vol. 39, No. 2, 1993, K. A. Erickson et al. describe a blood analyzer based on disposable IC biosensors that can quantify sodium, potassium, chloride, urea, nitrogen and glucose levels. A good overview of acoustic wave biosensors is provided by J. C. Andle et al. in Acoustic Wave Biosensors, published in the 1995 IEEE Ultrasonics Symposium Proceedings, IEEE cat. no. 0-7803-2940-6/95, pp. 451–460. Other types of IC biosensors are described in the art. However, it is sufficient for this disclosure to recognize that such IC sensors 220 are well known in the art and are generally available or readily fabricated for use on stents 222 or 222A (or other stent designs) as described above.

In the embodiments of FIGS. 19A through 19D, the implantable sensor IC 220 senses the concentration of a particular substance or another parameter that was determined to require monitoring prior to implanting the implantable sensor IC 220 or that is selected from a plurality of sensing capabilities provided on the implantable sensor IC 220 in response to control signals coupled via the RF coupling coil 223 or 223A. This diagnostic information is then used in conjunction with the therapeutic transducers of any of FIGS. 13 through 15, 17, 18, 20, 21 and 23 through 28.

Figure 20:
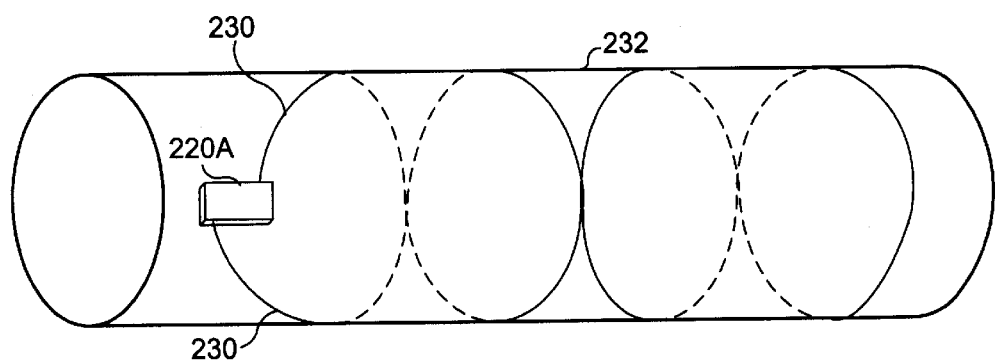
FIG. 20 is a side elevational schematic view showing an IC strain sensor and sensing filaments disposed on a stent.

A stent may include other types of sensors beside the ultrasonic transducers and the IC sensor 220 noted above. FIG. 20 illustrates an outline of a stent 232 that includes a strain sensor comprising strain sensing filaments 230 mounted on the stent 232. In the disclosed embodiment, strain sensing filaments 230 are wound around the stent 232 to measure displacement that is converted to a signal for transmission outside the body by an implantable IC 220A. The filaments 230 exhibit a change in electrical resistance with strain and are therefore usable to sense the strain experienced by the stent 232 when it is expanded inside a blood vessel. It is contemplated that the strain sensing filaments 230 be used only for strain sensing, so that their dimension, disposition and metallurgy can be optimized for that function. Alternatively, the strain sensing filaments 230 can comprise part of the structural body of the stent 232 so that they also provide a mechanical function related to the conventional function of the stent 232. It is also contemplated that strain gauges (not separately shown) can be used instead of the strain sensing filaments 230. The strain gauges can be mounted to the stent 232 at selected spaced-apart locations to measure displacement. Metallized polyimide substrate strain gauges are suited to this application, by wrapping the substrates around the body of the stent 232 and attaching the substrates to the body of the stent 232 at selected spaced-apart points. By monitoring the size of stent 232 as it is expanded, strain gauges or other strain measuring sensors can determine when a desired expansion of the stent 232 has been achieved. Alternatively, the strain data can be employed to assess the elasticity of the stent 232 and blood vessel structure by monitoring the dynamic strain over cardiac cycles, i.e., with successive systolic and diastolic pressure levels.

Figure 21B:
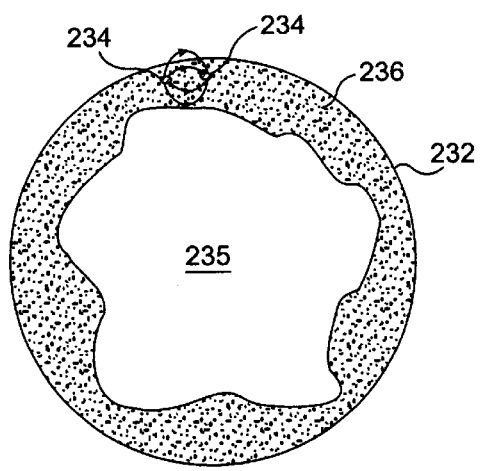
FIG. 21B is a cross-sectional view of a lumen of the stent in FIG. 21A, illustrating fatty tissue ingrowth.
Figure 21A:
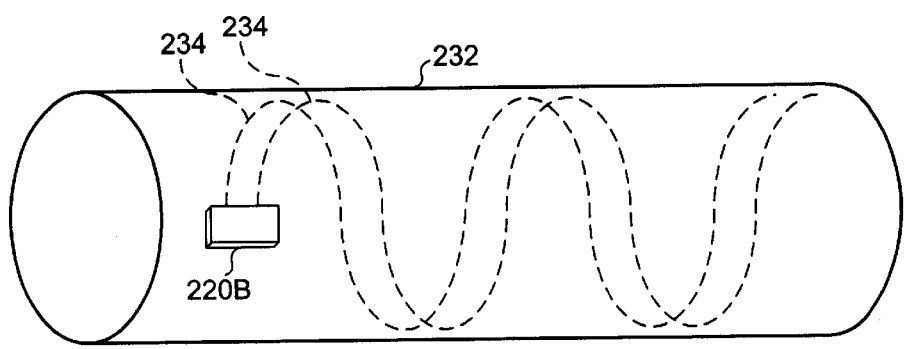
FIG. 21A is side elevational schematic view of a stent outline showing a deposit and ingrowth IC sensor and sensing filament.

Referring to FIG. 21A, an implantable IC sensor 220B that detects fatty deposits and tissue growth inside the lumen of the stent 232 is illustrated as being disposed within the body of the stent 232, coupled to a pair of dielectric sensing filaments 234. The implantable IC sensor 220B detects fatty deposits and tissue ingrowth within the lumen of the stent by measuring the dielectric and/or resistive properties of any material in contact with the sensing filaments 234, which are, e.g., helically coiled around the inner surface of the stent 232, from about one end of the stent 232 to its opposite longitudinal end. Alternatively, the sensing filaments 234 can be incorporated into the body or wall of the stent 232 itself. For example, when the stent 232 is fabricated with a woven mesh, a portion of the mesh can be utilized for making the dielectric and/or resistive measurement, while the remainder is used for a RF coupling coil.

In another embodiment, the sensing filaments 234 may be spatially more limited to allow assessment of where blockage is occurring within the stent 232. A plurality of localized sensing filaments 234 may permit assessment of more than one area within the stent 232, by taking a series of measurements and communicating the results of the series of measurements to the attending physician. This may provide data relevant to determining what form of treatment is appropriate.

For measuring the dielectric properties, the implantable IC sensor 220B is energized with power electromagnetically coupled from an external source into the RF coupling coil (not illustrated in FIG. 21A) of the stent 232 and produces signals indicative of tissue ingrowth that are electromagnetically coupled to the external monitoring system through the RF coupling coil of the stent 232. In one embodiment, an RF signal at a frequency of from 10 to 100 MHz is applied to the sensing filaments 234. At such frequencies, tissue has the properties shown in the following Table 1. FIG. 21B illustrates an exemplary cross section of a lumen 235 within the stent 232, showing the ingrowth of fatty tissue 236, which is in contact with the sensing filaments 234.

TABLE 1

| Tissue Type | Relative Permittivity | Resistivity (Ohm-cm) |
| --- | --- | --- |
| Fat | 6 to 20 | 2000 to 3000 |
| Blood | 80 to 160 | 80 to 90 |
| Muscle | 60 to 130 | 100 to 150 |

The permittivity of tissue is closely related to its water content. Water has a relative permittivity of about 80. Since fat and fatty deposits of the type found inside blood vessels contain much less water than other tissue types, the permittivity of fat is much lower than that of muscle or blood. The wall of a blood vessel is muscular and highly perfused and will therefore have a much higher permittivity than a fatty deposit. Similarly, fatty deposits have a much higher resistivity than either blood or muscle. Therefore, a measurement of the dielectric and/or resistive properties of tissue inside the stent 232 can differentiate fatty deposits from either blood or muscular tissue ingrowth into the lumen. The measurement can include a determination of capacitance, resistance or a combination of the two.

Further information can be obtained from the frequency dependence of the capacitance and resistance measured inside a stent lumen. For example, blood has a relatively flat resistivity vs. frequency characteristic curve, compared to that of muscle.

Figure 22:
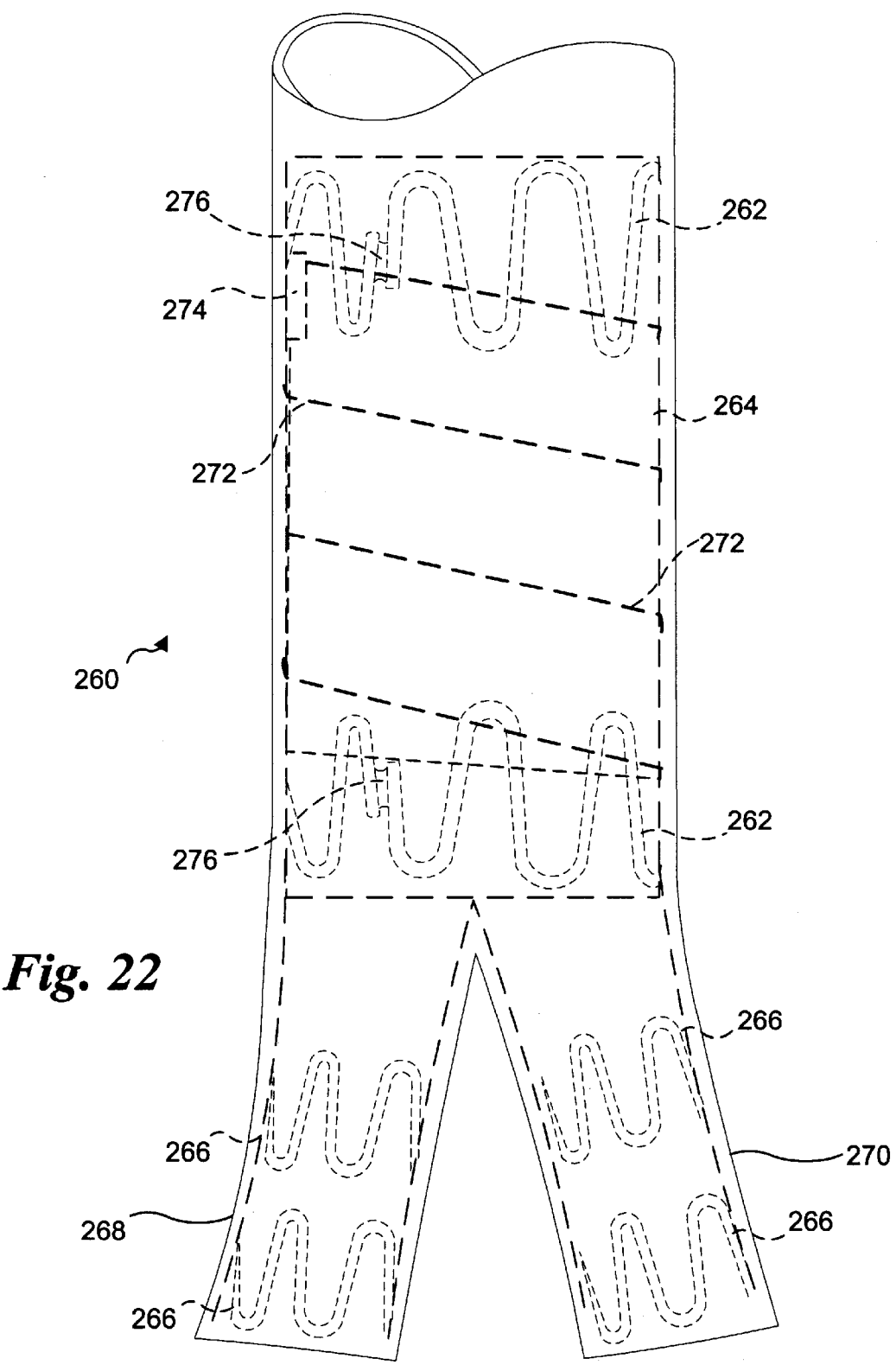
FIG. 22 is side elevational view of a portion of a branching artery in which a stent graft that is used for providing therapeutic functions is implanted.

FIG. 22 illustrates a stent graft (or spring graft) 260 that includes embodiments of the present invention. The stent graft 260 differs from a conventional synthetic graft in the method of delivery. Conventional grafts are installed surgically, while stent grafts 260 are installed using an endovascular delivery system. The entire stent graft 260 must be collapsible onto a delivery catheter (not shown). At a minimum, the stent graft 260 comprises a synthetic graft section 264 with an expandable stent 262 or 266 disposed at one or both ends. The stents 262 and 266 retain the synthetic graft section 264 in position. Some stent grafts 260 have stents 262 and 266 disposed along the entire length of the synthetic graft section 264, and some may include metal hooks at one or both ends to firmly attach the synthetic graft section 264 to the vessel wall.

The stent graft 260 is of a type that is used to repair arteries near a bifurcation of the artery into two small branches 268 and 270. However, it should be noted that the present invention can be used with almost any type of stent graft and is not in any way limited to the bifurcated type shown in the figure. The TALENT spring graft system available from World Medical Manufacturing is similar to the stent graft 260. The term "spring graft" is used with this type of stent graft 260 because the stent portions 262 and 266 may be self-expanding, comprising Nitinol springs acting as stents 262 and 266 that are embedded into polyester (DACRON™) or PTFE synthetic graft section 264. The larger diameter aortic section typically comprises DACRON and the smaller branch portions typically comprise PTFE. The material comprising the synthetic graft section 264 is stitched to the Nitinol stents 262. Although a Nitinol stent is normally self-expanding, a balloon (not shown) may be included in the delivery system to perform one or more functions, including expansion of the stent 262, placement at the desired location, flow occlusion and straightening blood vessels to aid advancement of the assembly to the desired location. Electrically insulating ceramic joints 276 couple sections of each stent 262 and 266 to break any current loop that could reduce the efficiency of the RF coupling coil. An insulated wire 272 is wound around the outside of the graft 264 and, in one embodiment, is formed of kinked or zigzag wire to enable expansion of the graft 264. The wire 272 is coupled to a sensor/electronic circuit 274. Stent grafts suitable for use in the embodiment shown in FIG. 22 are made by Sulzer Vascutek and W. L. Gore. The ANEURX stent graft from Medtronic, and the WALLGRAFT stent graft from Medivent-Schneider, which includes a woven mesh stent within its wall, are also suitable for this embodiment.

Description of Therapeutic Transducers

A variety of therapeutic transducers may be implanted that are responsive to and/or powered by the signals coupled into the implantable electronic circuits of FIGS. 1 through 6. One class of therapeutic transducers 44–46 provide utility by enabling localized delivery or activation of specific drugs for specific purposes. Two distinct applications where therapeutic transducers implanted within endoluminal implants provide therapeutic advantages are as adjunctive therapy and as primary therapy.

In adjunctive therapy, the therapeutic transducer is intended to realize localized drug activation and delivery in the vicinity of the stent or stent graft. This could be to maintain flow capability through the lumen by reducing restenosis due to new deposits of atherosclerotic material or to inhibit tissue ingrowth. Alternatively, in at least some cases, the same therapeutic transducer may aid in reducing thrombosis that is causing lumen blockage by activating appropriate drugs.

In primary therapy, the stent with the therapeutic transducer is implanted specifically to provide local drug activation and delivery to tissue in the vicinity of and downstream from the stent. For example, a stent could be implanted in an artery that feeds blood to a tumor site. Systemically administered chemotherapeutic agents that are not toxic until activated may be activated during passage through the stent by energy provided by the therapeutic transducer. The blood containing the activated drug then proceeds downstream to the tumor site to locally administer the activated drug. This approach can provide significantly greater drug concentrations at the tumor site than are obtained systemically. Similarly, other drugs used to treat a variety of diseases may be locally activated at the region of interest. In some cases, modified genetic material may be locally concentrated in response to therapeutic transducer activation.

One advantage to localized activation or delivery of drugs is that the side effects associated with the drugs may be reduced by only providing the drug at the site requiring treatment. This is advantageous in many situations, including chemotherapy, where the drugs are toxic or may have other potentially detrimental side effects.

For example, drug activation phenomena have been reported using ultrasound to break precursor substances down into drug molecules and other by-products. In this case, one or more of the transducers 44–46 of FIGS. 1 through 6 are ultrasonic transducers, several of which are described with respect to FIGS. 13 through 18. Sonochemical activation of hematoporphyrin for tumor treatment is described by S. I. Umemura et al. in *Sonodynamic Activation of Hematoporphyrin: A Potential Modality For Tumor Treatment,* published in the 1989 IEEE Ultrasonics Symposium Proceedings, IEEE cat. no. 0090-5607/89/0000-0955, pp. 955–960. Ultrasonic potentiation of adriamycin using pulsed ultrasound is described by G. H. Harrison et al. in *Effect Of Ultrasonic Exposure Time And Burst Frequency On The Enhancement Of Chemotherapy By Low-Level Ultrasound,* published in the 1992 IEEE Ultrasonics Symposium Proceedings, IEEE cat. no. 1051-0117/92/0000-1245, pp. 1245–1248. Similarly, increased toxicity of dimethlyformamide has been reported in conjunction with ultrasound by R. J. Jeffers et al. in *Enhanced Cytotoxicity Of Dimethylformamide By Ultrasound In Vitro,* published in the 1992 IEEE Ultrasonics Symposium Proceedings, IEEE cat. no. 1051-0117/92/0000-1241, pp. 1241–1244.

Sonodynamic activation at one or more specific body sites to provide local drug delivery is possible when one or more of the transducers 44–46 of FIGS. 1 through 6 are designed to provide suitable ultrasonic signals and are implanted at the locations where drug activation provides therapeutic benefits. Sonodynamic effects are nonlinear effects associated with the peak compression and expansion portions of the wave cycle; at lower frequencies, the time that the peak portions of the wave have to act is greater. For this reason, lower frequencies are preferred in some embodiments. Other embodiments increase peak forces by combining two or more ultrasonic waves. Several such transducers are described in connection with FIGS. 23 and 24 below.

Figure 23:
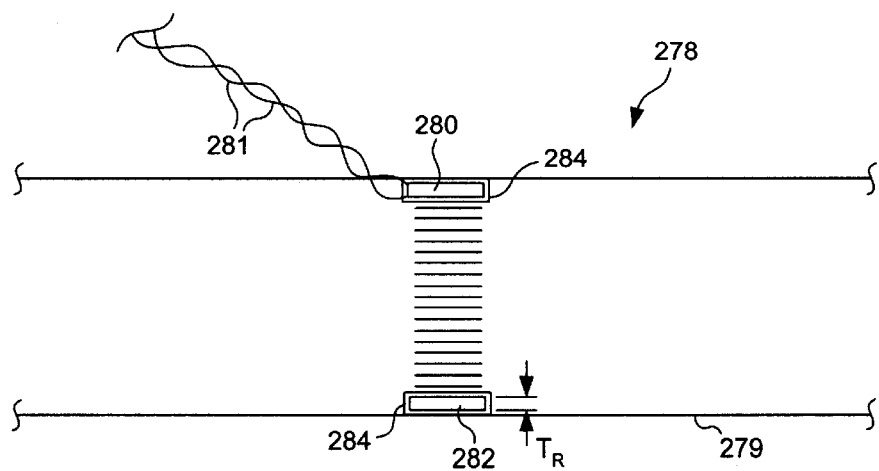
FIG. 23 illustrates an ultrasonic transducer configuration integrated with a stent or stent graft.

FIG. 23 illustrates an ultrasonic transducer configuration 278 integrated with a stent 279. The ultrasonic transducer configuration 278 is specifically designed to provide sonodynamic therapy via standing waves providing sonochemical activation of blood-borne drug precursors. This occurs in response to control signals coupled from the implantable electronic circuitry of FIGS. 1 through 6 by lines 281. The ultrasonic transducer configuration 278 is useful where local drug activation is desired in order to deliver the drug to the vessel having the stent 279 therein. The ultrasonic transducer configuration 278 is also useful when the downstream vasculature or an organ or tumor that is supplied blood via the downstream vasculature is the intended target for the activated drug.

The stent 279 includes an implantable ultrasonic transducer 280 on a first surface and a device 282 on a second surface. The device 282 may be either another ultrasonic transducer similar to the transducer 280 or an acoustic reflector. The ultrasonic transducer 280 may be coupled to implantable electronic circuits using any of the approaches described in connection with FIGS. 1 through 6. In one embodiment, the layer structure described in connection with FIG. 17 is applicable to the transducer 280. The standing acoustic wave, represented by the dashed parallel lines in FIG. 23, that is realized between the transducer 280 and the device 282 results in greater peak acoustic field strength for a given input energy level, which increases the rate of sonochemical drug activation and reduces the power levels required for sonochemical drug activation. Peak acoustic pressure increases of three- to five-fold are likely in most clinical settings.

The piezoelectric material forming the transducer 280 may comprise piezoelectric plastic materials such as PVDF, P(VCN/VAc) or P(VDF-TrFE), available from AMP Sensors of Valley Forge, Pa., or any of the piezoelectric ceramics, e.g., lead zirconium titanate. In one embodiment, PZT-4 material available from Morgan-Matroc of Bedford, Ohio provides high electroacoustic coupling and low acoustic losses. In another embodiment, the piezoelectric plastic P(VDF-TrFE) provides high electroacoustic coupling and low acoustic losses.

The transducer 280 (and, when the device 282 is a transducer, the device 282) may be of the type described, for example, with respect to FIGS. 13 through 18, or may be a slab type ultrasonic transducer, or may be similar to that shown and described in connection with FIG. 24, described below. In this application, the alignment between the transducer 280 and the device 282 must be maintained in order to preserve parallelism of the surface of transducer 280 that surfaces the device 282 and the surface of the device 282 that faces the transducer 280. It is also important to keep these surfaces opposed to each other, i.e., relative lateral motion of the transducer 280 and the device 282 must be inhibited. The result of maintaining this alignment is to form an acoustic cavity analogous to an optical Fabry-Perot resonator.

FIG. 23 also shows biocompatible coatings 284 surrounding both the transducer 280 and the device 282. The biocompatible coatings 284 are analogous to the biocompatible outer coating 192 of FIG. 17. The transducer 280 may also include an acoustic backing analogous to the acoustic backing 194 of FIG. 17, disposed on the transducer 280 as described in conjunction with FIG. 17. When an acoustic backing is employed with the transducer 280 (or in the device 282), it is important that the surface of transducer 280 that faces the device 282 (and the surface of the device 282 that faces the transducer 280) not be coated with the acoustic backing material.

When the device 282 is chosen to be an acoustic reflector, either a low impedance reflector (ie., providing an acoustic reflection coefficient approaching −1) or a high impedance reflector (i.e., providing an acoustic reflection coefficient approaching +1) may be employed. Low-density foams (e.g., analogous to the acoustic backing material 194 of FIG. 17) or aerogels provide low acoustic impedances suitable for use in acoustic reflectors, while rigid bodies such as metals or ceramics provide high acoustic impedances suitable for use in acoustic reflectors. Setting the thickness $T_R$ of the acoustic reflector to be an odd multiple of one quarter of an acoustic wavelength, as measured in the acoustic reflector material, increases the reflection coefficient of the acoustic reflector.

Alternatively, methods for localized delivery of medication include encapsulation of medications in delivery vehicles such as microbubbles, microspheres or microballoons, which may be ruptured to locally release the medications via localized energy provided by implanted transducers. In some embodiments, the delivery vehicles may include magnetic material, permitting the delivery vehicles to be localized via an applied magnetic field, as described in U.S. Pat. No. 4,331,654 entitled Magnetically-Localizable, Biodegradable Lipid Microspheres.

In one embodiment, the device 282 is formed from a magnetic ceramic or a magnetic metal alloy, and is also capable of acting as an efficient acoustic reflector. This embodiment allows localization of magnetic delivery vehicles via the static magnetic field associated with the device 282, followed by insonification of the delivery vehicles when appropriate via ultrasound emitted by the transducer 280 in response to signals from any of the implantable electronic circuits shown in FIGS. 1 through 6. As used herein, the term "insonify" means "expose to sound" or "expose to ultrasound"; "insonification" is used to mean exposure to sound or ultrasound. Insonification of delivery vehicles can provide localized heating, can rupture microbubbles to locally release drugs or drug precursors contained in the delivery vehicles or can trigger sonodynamic activation of drug precursors that are blood-borne or that are released when the delivery vehicles rupture. Microbubbles containing antistenotic agents are described, for example, by R. L. Wilensky et al. in *Microspheres*, Semin. Intervent. Cardiol., 1: 48–50, 1996. Microbubbles of various compositions and filled with various drugs are developed and manufactured by ImaRx Pharmaceutical Corp. of Tucson Ariz. An advantage that is provided by use of an implanted permanent magnet for localization of magnetic delivery vehicles in this embodiment and others is that permanent magnets do not require a rechargeable energy source in order to function. In some embodiments, this can provide a way of reducing power needs from the RF-to-DC power supply 32 of FIGS. 1 through 6.

The frequency of the ultrasound from the therapeutic transducer can be varied to enhance or to reduce cavitation resulting from the ultrasound emitted from the transducer. Suppression of cavitation via frequency modulation is described in U.S. Pat. No. 5,694,936 entitled "Ultrasonic Apparatus For Thermotherapy With Variable Frequency For Suppressing Cavitation." Methods for suppression or enhancement of cavitation are described in U.S. Pat. No. 4,689,986 entitled "Variable Frequency Gas-Bubble-Manipulating Apparatus And Method." Enhancing cavitation to enhance sonodynamic activation, rupture of microspheres, microballoons or microbubbles, to locally heat tissue or to destroy tissue is possible by causing the frequency of the emitted ultrasound to decrease with time. On the other hand, cavitation may be decreased by causing the frequency of the emitted ultrasound to increase with time. This may be used to limit tissue damage while still supplying sufficient ultrasound to accomplish, e.g., a diagnostic purpose.

Sonodynamic activation of drugs or sonically-induced delivery vehicles rupture may occur at reduced power levels when properly-phased collinear acoustic signals at two different frequencies are provided. This effect has been shown to be particularly advantageous when one signal is at a frequency that is the second harmonic of the other signal and the two signals have an appropriate phase relationship. Increased tissue damage for a given intensity of ultrasound has also been reported by S. I. Umemura in *Effect Of Second-Harmonic Phase On Producing Sonodynamic Tissue Damage,* published in the 1996 IEEE Ultrasonics Symposium Proceedings, IEEE cat. no. 0-7803-3615-1/96, pp. 1313–1318. Sonochemical activation of a gallium-deuteroporphyrin complex (ATX-70) at reduced total power density by use of properly phased signals comprising a first signal and a second signal at twice the frequency of the first signal is described by S. I. Umemura et al. in *Sonodynamic Approach To Tumor Treatment,* published in the 1992 IEEE Ultrasonics Symposium Proceedings, IEEE cat. no. 1051-0117/92/0000-1231, pp. 1231–1240. An example of a transducer that is designed to provide for transduction of two ultrasonic signals, one of which may be the second harmonic of the other, is now described with reference to FIG. 24.

Figure 24:
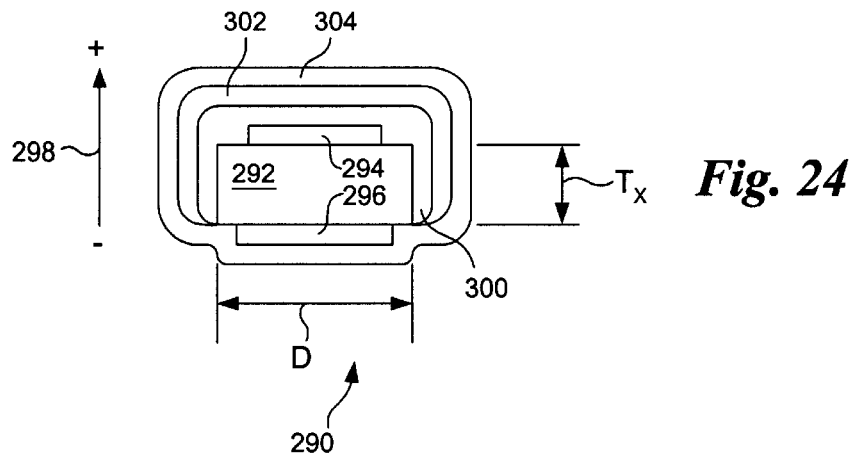
FIG. 24 illustrates an embodiment of a dual frequency ultrasonic transducer.

FIG. 24 illustrates an embodiment of a dual frequency ultrasonic transducer 290. The dual frequency transducer 290 is designed to provide two different frequencies of collinearly propagating ultrasound, where one of the frequencies may be the second harmonic of the fundamental transducer frequency, when supplied with suitable electrical signals. The phases of the two signals may be adjusted by the implantable electronic circuit of FIGS. 4 through 6 and this may be in response to signals from the power supply and patient monitoring console 101 of FIG. 12. The dual frequency transducer 290 comprises a disc 292 of piezoelectric material, poled, for example, as indicated by direction arrow 298. The disc 292 has a diameter D and a thickness $T_X$. Electrode 294 and electrode 296 are formed on opposed surfaces of the disc 292 as described in conjunction with the rear and front electrodes 196 and 200 of FIG. 17 above.

In one embodiment, the diameter D is chosen to provide the desired fundamental transducer frequency via radial mode coupling, while the thickness $T_X$ is chosen to provide the second harmonic of the fundamental transducer frequency via thickness mode coupling. In this case, the diameter to thickness ratio $D/T_X$ may be approximately 2:1. Conventional mode charts provide more precise ratios for a variety of materials. The radial mode comprises radial particle motion primarily into and out from the center of the disc, i.e., perpendicular to the direction arrow 298, and symmetric about a cylindrical axis of the disc 292. The surfaces of the disc 292 exhibit longitudinal motion (i.e., parallel to the direction arrow 298) in response to the radial mode oscillation because of the Poisson's ratio of the material. The thickness mode comprises particle motion parallel to the direction arrow 298. As a result, acoustic energy propagating in the same direction at both frequencies may be coupled out of the disc 292 via the surfaces on which the electrodes 294 and 296 are formed. In some embodiments, the acoustic radiating surface emitting the ultrasound does not include an electrode 294 or 296. For example, electrodes may be disposed on the sidewalls, with ultrasound being emitted from the planar surfaces.

In another embodiment, the radial mode providing ultrasound at the fundamental transducer frequency may be chosen to be a harmonic of the lowest radial mode of the transducer 290. The transducer 290 may then be designed to have a larger diameter D than is possible when the lowest radial mode corresponds to the fundamental transducer frequency. This allows a larger area to be insonified by both ultrasonic signals than is otherwise feasible.

In one embodiment, frequencies of 500 kHz and 1 MHz are chosen as the two output frequencies for the dual frequency transducer 290. When the disc 292 comprises lead zirconium titanate (PZT), the diameter D is about 4 mm and the thickness $T_X$ is about 2 mm. The resulting dual frequency transducer 290 is small enough to be incorporated in an implantable device and yet also large enough to insonify a significant portion of the lumen of many blood vessels or stents.

In an alternative embodiment, a rectangular slab may be substituted for the disc 292. In one embodiment, a lateral mode may then be used instead of the radial mode associated with the disc 292 to provide the resonance at the fundamental frequency, with the thickness mode providing the resonance at the second harmonic. Conventional mode charts are used to select the ratios of the relevant dimensions.

Coating a cylindrical sidewall of the disc 292 and one of the electrodes 294 and 296 with an acoustic isolator 300 (analogous to the acoustic backing 194 of FIG. 17) allows the other of the electrodes 294 and 296 to serve as an acoustic radiator. Choosing the acoustic isolator 300 to have a low relative dielectric constant reduces capacitive loading of the dual frequency transducer 290 by the patient's body, which, as noted above, has a high relative dielectric constant (approaching 80) and which also includes conductive solutions. Coating the acoustic isolator 300 with a grounded conductor 302, selecting the electrode 296 to be a grounded electrode and selecting the electrode 294 to be a driven electrode reduces unwanted radiation of electromagnetic signals from the transducer 292. A thin biocompatible coating 304 (analogous to the outer coating 192 of FIG. 17) protects the dual frequency transducer 290 from exposure to biological matter without preventing radiation of ultrasound from the surface bearing the electrode 296.

Other types of localized therapy include coupling a thermally-activated medication to carrier molecules that have affinity to tumor tissue. Localized heating of the tumor tissue enables selective activation of the medication in the tumor tissue, as described in U.S. Pat. No. 5,490,840 entitled Targeted Thermal Release Of Drug-Polymer Conjugates. Localized heating may be effected through ultrasound via an ultrasonic transducer, e.g., transducers 44–46 (FIGS. 1 through 6) implanted to allow insonification of the affected area. Higher acoustic frequencies provide shorter penetration depths, i.e., provide greater control over where the ultrasound and therefore the resultant heat is delivered. Additionally, heating is increased by ultrasonic cavitation in the presence of microbubbles, microspheres or microballoons. Other methods for providing localized magnetic forces or heating include electromagnetic or resistive heating transducers 44–46 comprising coils.

Figure 25:
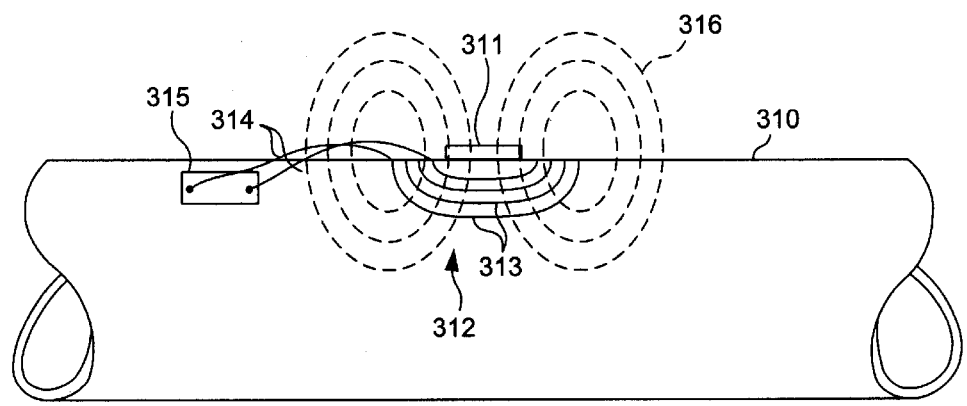
FIG. 25 illustrates one embodiment of a coil integrated into a stent.

FIG. 25 illustrates a coil 312 integrated into a stent 310. The coil 312 comprises saddle-shaped wires 313 integrated into the stent 310. The coil 312 may be an electromagnetic transducer used to magnetically capture delivery vehicles bearing drugs. Leads 314 couple the coil 312 to an implantable control IC 315, which may comprise the implantable electronic circuits of any of FIGS. 1 through 6. The implantable electronic circuits of FIGS. 4 through 6 may provide advantages in this situation because the frequency of the signal providing power to the implantable electronic circuits may be different from the frequency of the signals to the transducers 44–46, such as the coil 312. This may avoid a situation where the signals providing power to the implantable electronic circuits also result in release of drugs in the vicinity of the RF coupling coil 30 that is receiving the electrical power.

When a suitable current, either AC or DC, is supplied via the leads 314, a magnetic field represented by flux lines 316 is generated. The magnetic field captures magnetic delivery vehicles that have been introduced into the patient's bloodstream. The increased concentration of delivery vehicles in the target vicinity can be used to provide local increases in delivery of drugs contained in the delivery vehicles.

Microbubbles including medication may be localized via a magnetic field and ruptured via an oscillating magnetic field as described in U.S. Pat. No. 4,652,257 entitled Magnetically-Localizable, Polymerized Lipid Vesicles And Method Of Disrupting Same. Suitable magnetic fields may be provided via application of RF or RF and DC electrical energy to the coil 312. In these embodiments, one or more of the transducers 44–46 of FIGS. 1 through 6 comprise the coil structure 312. In response to signals coupled to the implantable electronic circuit, the transducer 44–46 that is selected is activated and is supplied with current to either trap the magnetic delivery vehicles so that they can be ruptured via signals provided from another selected transducer 44–46 (e.g., an ultrasonic transducer that ruptures microbubbles, microspheres or microballoons via cavitation), or an oscillating magnetic field may be superposed on the magnetic fields generated by the coil 312 used to trap the delivery vehicles.

Referring again to FIG. 25, in another embodiment, a permanent magnet 311 may be included on or in the stent 310 to provide a static magnetic field for localization of magnetic delivery vehicles. An oscillating magnetic field may then be provided via signals supplied to the coil 312 to rupture the delivery vehicles under the control of the implantable electronic circuit of any of FIGS. 1 through 6, where the coil 312 acts as one of the transducers 44–46. These embodiments may reduce power requirements for the implantable control IC 315 while retaining external control over when the drug or drug precursor is released via signals from the power supply and patient monitoring console 101 of FIG. 12. Other types of coils, e.g., analogous to the RF coupling coils 30B, 30C or 30D of FIGS. 7 through 10, or 121 of FIGS. 11A and 11B, may also be used instead of the RF coupling coil 312.

Figure 26:
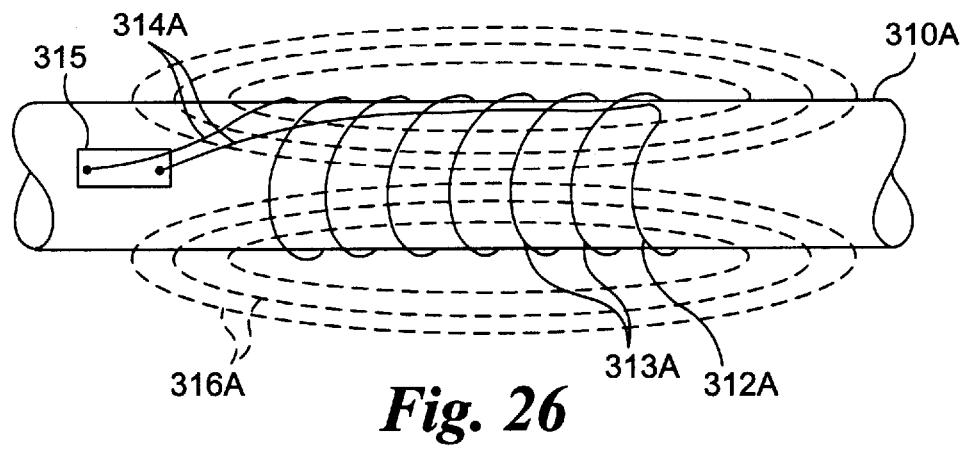
FIG. 26 illustrates another embodiment of a coil integrated into a stent.

FIG. 26 illustrates another embodiment of a coil 312A integrated into a stent 310A. The coil 312A is analogous to the coil 312 of FIG. 25, but is shaped as a cylindrical coil rather than as a saddle-shaped spiral. Leads 314A couple wires 313A comprising the coil 312A to an implantable control IC 315A, which is analogous to the implantable control IC 315 of FIG. 25. When a suitable current, either AC or DC, is supplied via the leads 314A, a magnetic field represented by flux lines 316A is generated. The coil 312A may be used to capture magnetic delivery vehicles that have been introduced into the patient's bloodstream.

In other embodiments, the coils 312 or 312A may form resistive heating transducers comprising a resistive material and may, if desired, be wound with bifilar wire to prevent them from acting as electromagnets or RF coupling coils. In another embodiment, the coils 312 or 312A may be heated directly by magnetic fields inducing current in the coils 312 or 312A, or, the body of the stent 310A may form a resistive heating transducer that is heated via magnetically-induced currents.

Stents are typically fashioned from metals that are biocompatible, such as titanium alloys (e.g., Nitinol, a nickel titanium alloy), stainless steel (e.g., 316L), platinum/iridium alloys or tantalum. All of these materials are suitable for fashioning a stent that is to be directly heated by RF-induced eddy currents (such stents would not include slots such as slot 118, FIG. 11A, or insulating couplings such as 119, FIG. 11A, or 146, FIG. 11B), however, titanium and Nitinol have the highest electrical resistivity, while platinum/iridium and tantalum have the lowest electrical resistivity. When a stent body is to be directly heated by induced eddy currents, titanium or Nitinol may present advantages.

When a RF coupling coil is to be fashioned from these materials, those applications with higher power requirements may favor the materials with the lower resistivities.

When a current is passed through coils analogous to RF coupling coils 312 or 312A but comprising resistive material, or through a stent body as eddy currents, a local temperature rise is produced. This local temperature rise may be employed to rupture microbubbles having a melting point slightly above normal human body temperatures. One system using microbubbles having a controlled melting point to facilitate rupture of the microbubbles at predetermined localized areas within a patient's body is described, for example, in U.S. Pat. No. 4,558,690 entitled Method Of Administration Of Chemotherapy To Tumors. The localized heating may be provided by a structure similar to the cylindrical RF coupling coil 30A of FIG. 7, the woven mesh coils 30B and 30C of FIGS. 8 and 9, the saddle RF coupling coil 30D of FIG. 10, the RF coupling coil 121 of FIGS. 11A and 11B, the coil 312 of FIG. 25 or the coil 312A of FIG. 26, with the conductors of the coils comprising a suitably resistive material such as nichrome wire. The heating may be supplied directly by RF excitation of the coils 30A through 30D or 121, or it may be effected via the implantable electronic circuits of FIGS. 1 through 6. This may be in response to signals from the power supply and patient monitoring console 101 of FIG. 12. Additionally, delivery vehicles such as microbubbles, microspheres or microballoons can increase localized heating of tissue via rupture of the delivery vehicles caused by localized application of ultrasound, as discussed, for example, in *Technical Report: Drug And Gene Delivery,* Jul. 2, 1997, ImaRx Pharmaceutical Corp.

Transducers may be employed to facilitate drug penetration through the wall of a stent or stent graft and into the surrounding vasculature via sonophoresis, i.e., ultrasound enhancement of drug penetration into body tissues, or via iontophoresis, i.e., electrical field enhancement of drug penetration into body tissues, when suitable transducers are included in the stent or stent graft.

Methods and apparatus for localized drug delivery via sonophoresis or phonophoresis are described in U.S. Pat. No. 4,484,569 entitled Ultrasonic Diagnostic And Therapeutic Transducer Assembly And Method For Using, U.S. Pat. No. 5,016,615 entitled Local Application Of Medication With Ultrasound and U.S. Pat. No. 5,267,985 entitled Drug Delivery By Multiple Frequency Phonophoresis. These patents generally discuss transdermal delivery of medication to an affected area and note that use of more than one frequency of ultrasonic energy is beneficial in some situations.

An iontophoretic catheter for drug delivery is described in *Iontophoretic Drug Delivery System,* by R. G. Welsh et al., Semin. Intervent. Cardiol., No. 1, pp. 40–42 (1996). The system uses a microporous membrane enclosing a drug solution and a drug delivery electrode. A reference electrode is coupled to the biological tissue at a site that is separate from the drug delivery electrode. The reference and drug delivery electrodes are coupled to a power supply that provides an electrical potential between the two electrodes. Cationic drugs move from the anode towards the cathode, while anionic drugs move from the cathode towards the anode, with the rate being generally proportional to the current. Control over localized drug delivery is effected via control of the current and the duration of the current from the drug delivery electrode. One application is for delivery of antirestenotic agents.

Other uses of iontophoresis are described in U.S. Pat. No. 4,383,529 entitled Iontophoretic Electrode Device, Method and Gel Insert and U.S. Pat. No. 4,416,274 entitled Ion Mobility Limiting Iontophoretic Bioelectrode. These generally describe iontophoretic apparatus for localized transdermal drug delivery. Catheters adapted to provide localized iontophoretic drug delivery are described in U.S. Pat. No. 4,411,648 entitled Iontophoretic Catheter Device, and U.S. Pat. No. 5,499,971 entitled Method For Iontophoretically Delivering Drug Adjacent To A Heart. These discuss specific problems that are most readily addressed via localized drug delivery, including treatment of vascular regions to reduce restenosis following PTCA, drug delivery to tumor sites and techniques for iontophoretically delivering drugs in the vicinity of the heart without inducing arrhythmia due to electrical stimulation of heart muscles and nerves. In one embodiment, this is effected together with provision of electrical fields effective in providing drug transport by chopping a DC potential difference at a rate of between 5 and 15 kHz or by providing an asymmetric AC waveform that is in this frequency range. These techniques are necessary because the current being used for iontophoresis travels through a significant and somewhat unpredictable amount of body tissue that may well include muscles and nerves associated with the heart.

These concepts become more powerful when combined with the implantable transducers 44–46 of FIGS. 4 through 6 for providing the energy to locally deliver or locally activate the medications. An example of an iontophoretic transducer is described in conjunction with FIG. 27 below.

Figure 27:
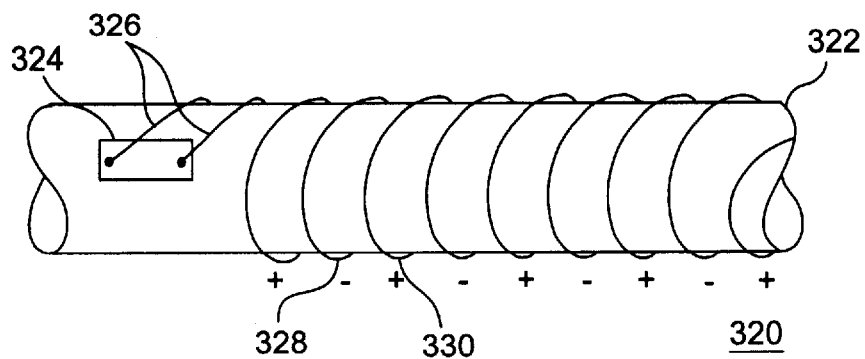
FIG. 27 illustrates an embodiment of an iontophoretic system for local drug delivery.

FIG. 27 illustrates an embodiment of an iontophoretic system 320 for local drug delivery in the vicinity of an implanted stent 322. The iontophoretic system 320 includes an implantable control IC 324, which may be coupled to the stent 322. The implantable control IC 324 is coupled via wires 326 to a first electrode 328 and to a second electrode 330. The first 328 and second 330 electrodes are insulated from the stent 322 when the stent 322 comprises conductive material, unless the stent 322 comprises one of the electrodes 328 and 330. The first 328 and second 330 electrodes comprising an iontophoretic transducer may be disposed on the exterior of the stent 322 (as illustrated), on the interior of the stent 322, or may be disposed such that one is inside the stent 322 and the other is external to the stent 322.

A potential difference is established between the first 328 and second 330 electrodes by the implantable control IC 324 in response to signals coupled from outside the patient's body, via a RF coupling coil (not illustrated) as discussed above. The potential difference causes some types of drugs to migrate from one of the electrodes 328 and 330 towards the other, according to the polarity of the potential difference and the specific nature of the drug. This effect may be used to provide localized drug therapy, for example, to the wall of the vessel (not illustrated) into which the stent 322 is implanted. For example, systemically-administered drugs may be selectively transported from the blood into the vasculature surrounding a stent 322 to provide increased local concentrations of antistenotic agents.

One advantage of this technique is that the currents produced by the iontophoretic system 320 are extremely localized, i.e., are substantially confined to the area between the electrodes 328 and 330 and immediately surrounding tissues. This obviates some of the problems that have been encountered with iontophoretic systems that use a reference electrode that is placed at a body location remote from the drug delivery electrode, e.g., a catheterized drug delivery electrode used in conjunction with an externally-applied reference electrode. Accordingly, the iontophoretic system 320 may employ a DC voltage to effect iontophoretic drug delivery to parts of the body that cannot safely be treated via a catheterized system using DC for iontophoretic drug delivery. This is advantageous in improving the efficiency of drug delivery and in reducing exposure of other portions of the body to the electrical currents being employed for iontophoresis. One area where this may provide advantages, depending on stent placement and other factors, is in treating restenosis of cardiac blood vessels following stent insertion as a part of a PTCA treatment. A stent 322 intended for this purpose may also include sensors providing signals indicative of blood flow through the stent and therefore capable of providing data indicative of blockage as it develops. Additionally, the stent 322 including iontophoretic electrodes 328 and 330 may also be used to enhance localized delivery of drugs that are activated via therapeutic transducers coupled to the stent 322 or that are included in the vasculature upstream of the stent 322.

Another method for localized drug activation uses light supplied by an optical transducer, where the light is of the appropriate wavelength and intensity to break precursor molecules down into drugs. U.S. Pat. No. 5,445,608 entitled Method And Apparatus For Providing Light-Activated Therapy, describes a photodynamic therapy achieved by photoactivation of suitable optically active drugs. As described in this patent, the drugs are activated via catheterized light emitters inserted at the site to be treated and providing light at the wavelength required in order to activate the drugs and at the location where the activated drugs are needed for therapeutic purposes. Examples of precursor substances that can be optically activated by being broken down into drug molecules include long-chain cyanine dyes, dimers of phthalocyanine dyes and porphyrin compounds. A wide selection of solid state light sources including laser diodes and light emitting diodes is commercially available from a variety of vendors, including Motorola of Phoenix, Ariz. Laser diodes or light emitting diodes may be employed as transducers 44–46 in any of the systems shown in FIGS. 1 through 6 to provide light for photoactivation of drugs within a patient's body via signals from the implantable electronic circuit in response to signals transmitted from the power supply and patient monitoring console 101 of FIG. 12.

Figure 28:
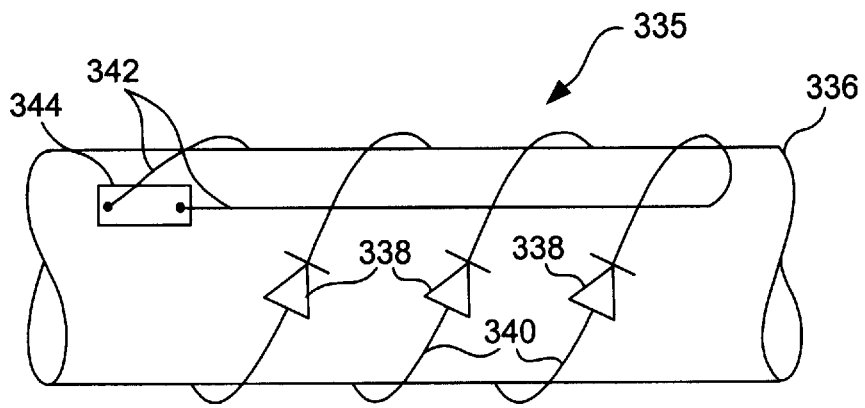
FIG. 28 illustrates an embodiment wherein light emitting transducers are coupled to a stent.

FIG. 28 illustrates an embodiment wherein light emitting or optical transducers 338 are coupled to a stent 336. The light emitting transducers 338 may comprise light emitting diodes having an appropriate wavelength or may comprise diode lasers. The light emitting transducers 338 may be coupled in series via lines 340, as shown in FIG. 28, or may be coupled in parallel. When the light emitting transducers 338 are coupled in series, one disadvantage is that catastrophic failure of one of the light emitting transducers 338 that causes the failed light emitting transducer 338 to fail to pass enough current for light emission may also prevent the remainder of the light emitting transducers 338 from operating.

The light emitting transducers 338 are coupled via lines 342 to an implantable control IC 344, which is in turn coupled to a RF coupling coil (not illustrated in FIG. 28) that provides energy and control signals. The light emitting transducers 338 may be disposed on the outside of the stent 336, as shown, or on the inside of the stent 336 or both as required for a given application.

The transducers 44–46 of FIGS. 1 through 6 may concentrate or activate medications by supplying heat, via resistive processes or insonification, or may employ light, magnetic fields or electrical fields for localized drug delivery or activation. The ultrasonic transducer 290 of FIG. 24 is, among other ultrasonic transducers, also suited to increasing drug penetration of drugs via sonophoresis into, e.g., tumors or vascular walls via an implantable electronic circuit such as any of those shown in FIGS. 4 through 6.

An example of an application for the systems described above occurs in the situation where a stent is implanted to correct a stenosis or to repair an aneurysm in a blood vessel. Over time, tissue ingrowth at the ends of the stent can lead to stenosis, which can lead to thrombus formation. Thrombosis threatens the viability of the stent, and may require aggressive intervention using surgery or drugs. It is very undesirable to have to surgically resolve this situation if there is a viable alternative approach for relieving the blockage. One approach is to infuse the patient with thrombolytic drugs. This may lead to hemorrhagic consequences in other parts of the body, especially if the patient has, for example, recently had surgery. One approach to reducing the amount of thrombolytic drugs required to resolve thromboses in vitro is described in *Prototype Therapeutic Ultrasound Emitting Catheter For Accelerating Thrombolysis*, J. Ultrasound Med. 16, pp. 529–535 (1997). In this study, urokinase alone as a fibrinolytic agent was compared to urokinase in the presence of ultrasonic energy, with the latter showing marked improvement in the degree of fibrinolysis of artificial blood clots in glass tubes.

When, however, the stent includes a transducer, such as an ultrasonic transducer, coupled to the implantable electronic circuit of any of FIGS. 1 through 6, the introduction of a thrombolytic drug into the bloodstream of the patient can be followed by generation of ultrasound within the stent via the transducer and under the control of an attending physician. This allows the thrombolytic drug, e.g., urokinase, streptokinase or tissue plasminogen activator, to be activated at the site of the thrombus and under the control of the attending physician, reducing the probability of hemorrhagic consequences at portions of the patient's body remote from the site being treated. It also enables rapid onset of treatment, which can be critical in some situations, e.g., in the event of heart attack or stroke induced via thrombolysis, and may obviate invasive surgery in the event that the therapeutic transducer has already been implanted in a prior procedure.

Additionally, when flow or pressure sensors such as are described with respect to FIGS. 13 through 16 or 18 are also included with the stent when the stent is implanted and these are also coupled to the implantable electronic circuits of any of FIGS. 2 through 6, the attending physician may be able to obtain information that is indicative of graft condition. This can allow the physician to more readily determine if the condition is treatable without resorting to invasive evaluation and intervention. Monitoring during non-invasive treatment, e.g., local drug activation, accomplished through use of an implanted blood velocity or blood pressure transducer, may allow assessment of the progress of thrombolysis that may, in turn, permit successful noninvasive treatment without incurring undue risk to the patient.

Further, when stents are implanted to relieve stenosis, restenosis due to tissue ingrowth tends to occur within the first 6 months following angioplasty, with the greatest loss of luminal diameter occurring between the first and third month. Detection of tissue growth can be determined via pressure sensors as described above or via incorporation of the dielectric sensing filaments 234 and the implantable IC sensor 220B of FIGS. 21A and 21B. When the ultrasonic transducers, such as those of any of FIGS. 13–18, 23 or 24, are included in the upstream side of an implanted stent, precursor drugs activated sonodynamically may locally provide antistenotic agents such as colchicine, heparin, methotrexate, angiopeptin or hirudin to relieve or reduce restenosis without requiring systemic administration of the drugs. Alternatively, delivery vehicles ruptured via ultrasound may provide localized delivery of antistenotic agents. This provides a way of controlling restenosis on an as-needed basis as determined via the benefit of diagnostic data, under the control of a physician, and without requiring anesthesia or surgery. An advantage associated with at least some of the therapeutic transducers described herein is that they are not necessarily specific to one drug or condition. For example, ultrasonically activated therapy provides advantages in treatment of both restenosis and thromboses, either of which may threaten viability of an implanted stent.

From the foregoing it will be appreciated that, although specific embodiments of the invention have been described herein for purposes of illustration, various modifications may be made without deviating from the spirit and scope of the invention. Accordingly, the invention is to be understood broadly and is not limited except as by the appended claims.

What is claimed is:

1. An apparatus configured to be implanted in a lumen having a passageway, the apparatus comprising:
    an endoluminal implant adapted to be implanted within the passageway; and
    a transducer coupled to said endoluminal implant.

2. The apparatus of claim 1 wherein said transducer comprises a therapeutic transducer.

3. The apparatus of claim 1 wherein said transducer comprises a therapeutic transducer chosen from a group comprising: an electromagnetic transducer, an optical transducer, an ultrasonic transducer, a resistive heater transducer and an iontophoretic transducer.

4. The apparatus of claim 1, further comprising a RF coupling coil having an output coupled to said transducer.

5. The apparatus of claim 4, further comprising a RF-to-DC power supply electrically coupled to said output of said RF coupling coil and having an output coupled to a signal source that is in turn coupled to said transducer, said signal source activating said transducer in response to signals from said RF coupling coil.

6. The apparatus of claim 1 wherein said endoluminal implant is chosen from a group comprising: a stent and a stent graft.

7. The apparatus of claim 2 wherein said therapeutic transducer is coupled to a saddle-shaped coil integrated into a wall of said endoluminal implant.

8. The apparatus of claim 2 wherein said therapeutic transducer is coupled to a helical coil integrated into a wall of said endoluminal implant.

9. The apparatus of claim 4 wherein:
    said endoluminal implant comprises a stent; and
    said RF coupling coil comprises a woven mesh of wire integrated into a wall of said stent.

10. The apparatus of claim 9 wherein said woven mesh of wire comprises:
    a first set of coils of insulated wire each forming a right-handed spiral; and
    a second set of coils of insulated wire each forming a left-handed spiral, said second set of coils interwoven with said first set of coils, wherein said first set of coils and said second set of coils are electrically coupled in series in a daisy-chain configuration.

11. The apparatus of claim 9 wherein said woven mesh of wire comprises:
    a first set of coils of insulated wire each forming a right-handed spiral, each of said coils of said first set of coils having a first end and a second end, wherein said first ends are electrically coupled to each other and said second ends are coupled to each other; and
    a second set of coils of insulated wire each forming a left-handed spiral, said first and second sets of coils interwoven with each other to form said woven mesh, each of said coils of said second set of coils having a first end and a second end, wherein said first ends of said second set of coils are electrically coupled to each other and said second ends of said second set of coils are coupled to each other, said first and second sets of coils being electrically coupled to each other and to said transducer.

12. The apparatus of claim 2 wherein said therapeutic transducer includes a regular solid comprising piezoelectric material, wherein a first resonance frequency is determined by a first dimension of said regular solid and a second resonance frequency is determined by a second dimension of said regular solid, said regular solid including a first electrode coupled to a first surface of said regular solid and a second electrode coupled to a second surface of said regular solid.

13. The apparatus of claim 12, further comprising an acoustic isolator disposed on said first electrode and on a sidewall of said regular solid and wherein said first dimension is approximately twice said second dimension.

14. The apparatus of claim 2 wherein said therapeutic transducer comprises:
    an ultrasonic transducer having an acoustic radiating surface, wherein a first electrode and a second electrode are coupled to said ultrasonic transducer, said ultrasonic transducer coupled to a first wall of said endoluminal implant; and
    an acoustic reflector coupled to a second wall of said endoluminal implant, said acoustic reflector being maintained in alignment with and facing said acoustic radiating surface of said ultrasonic transducer by said endoluminal implant.

15. The apparatus of claim 14 wherein said acoustic reflector comprises a magnet.

16. The apparatus of claim 2 wherein said therapeutic transducer comprises:
    a first ultrasonic transducer having an acoustic radiating surface, wherein a first electrode and a second electrode are coupled to said first ultrasonic transducer, said first ultrasonic transducer coupled to a first wall of said endoluminal implant; and
    a second ultrasonic transducer having an acoustic radiating surface, wherein a first electrode and a second electrode are coupled to said second ultrasonic transducer, said second ultrasonic transducer being coupled to a second wall of said endoluminal implant such that said acoustic radiating surface of said first ultrasonic transducer is aligned with and facing said acoustic radiating surface of said second ultrasonic transducer.

17. The apparatus of claim 2, further comprising:
a RF coupling coil integrated into a wall of said endoluminal implant;
an implantable electronic circuit, said implantable electronic circuit including a RF-to-DC power supply circuit coupled to said RF coupling coil, whereby RF energy coupled into said RF coupling coil may be converted to DC power, and whereby RF coded information may be exchanged between said RF coupling coil; and said implantable electronic circuit.

18. The apparatus of claim 17, wherein said implantable electronic circuit also includes:
RF decoding circuitry and a multiplexer, said RF decoding circuitry coupled to said RF coupling coil, whereby said multiplexer may supply signals from said implantable electronic circuit to said therapeutic transducer; and
a second transducer coupled to said endoluminal implant wherein said first and second transducers are coupled to said implantable electronic circuit and comprise ultrasonic transducers configured to provide first and second acoustic waves in a space between said first and second transducers in response to signals from said implantable electronic circuit.

19. The apparatus of claim 2, further comprising a diagnostic transducer coupled to said endoluminal implant.

20. The apparatus of claim 19, wherein said diagnostic transducer provides signals indicative of a parameter describing a fluid flowing through said endoluminal implant, wherein said parameter is chosen from a list comprising: fluid flow, pressure, temperature and biochemical properties.

21. The apparatus of claim 4 wherein said therapeutic transducer includes a therapeutic transducer chosen from a group comprising: ultrasonic transducers, optical transducers, magnetic transducers, resistive heating transducers and iontophoretic transducers.

22. An apparatus configured to be implanted in a lumen having a passageway, the apparatus comprising:
an endoluminal implant adapted to be implanted within the passageway;
a RF coupling coil coupled to said endoluminal implant;
an implantable electronic circuit electrically coupled to said RF coupling coil and physically coupled to said endoluminal implant, said RF coupling coil for supplying electrical power to said implantable electronic circuit and for coupling control and data signals to and from said implantable electronic circuit; and
a therapeutic transducer electrically coupled to said implantable electronic circuit, said therapeutic transducer for delivering therapeutic energy to a lumen disposed within said endoluminal implant in response to said control signals.

23. The apparatus of claim 22 wherein said RF coupling coil is disposed on said endoluminal implant and comprises a RF coupling coil chosen from a group comprising: a saddle-shaped coil, a helical coil and a woven mesh coil.

24. The apparatus of claim 22 further comprising a diagnostic transducer coupled to said endoluminal implant, said diagnostic transducer electrically coupled to said implantable electronic circuit to provide diagnostic signals thereto.

25. The apparatus of claim 24 wherein said diagnostic transducer comprises a pressure transducer arranged to measure a pressure of a fluid in a lumen of said endoluminal implant.

26. The apparatus of claim 22 wherein said therapeutic transducer comprises means for insonifying a lumen disposed in said endoluminal implant.

27. The apparatus of claim 22 wherein said therapeutic transducer comprises means for insonifying a lumen disposed in said endoluminal implant with one or more acoustic waves.

28. The apparatus of claim 22, further comprising a diagnostic transducer coupled to said endoluminal implant, said diagnostic transducer including an electrical coupling to said implantable electronic circuit for exchanging data between said diagnostic transducer and said implantable electronic circuit.

29. The apparatus of claim 28 wherein said diagnostic transducer comprises a conformal transducer array coupled to said endoluminal implant to measure fluid velocity through a lumen extending through said endoluminal implant.

30. The apparatus of claim 28 wherein said diagnostic transducer comprises a first electrode and a second electrode, said first and second electrodes disposed in a fixed, spaced-apart relationship within a lumen of said endoluminal implant and adjacent a wall thereof, whereby capacitance or resistance measurements between said first and second electrodes characterize those bodily elements immediately surrounding said first and second electrodes.

31. The apparatus of claim 28 wherein said diagnostic transducer comprises a first pressure transducer disposed at an inlet whereby fluid enters said endoluminal implant.

32. The apparatus of claim 31 wherein said diagnostic transducer further comprises a second pressure transducer disposed at an outlet whereby fluid exits said endoluminal implant.

33. The apparatus of claim 22 wherein said therapeutic transducer includes one or more light sources.

34. The apparatus of claim 22 wherein said therapeutic transducer comprises an iontophoretic transducer.

35. The apparatus of claim 22 wherein said therapeutic transducer comprises an electromagnetic transducer.

36. The apparatus of claim 22 wherein said therapeutic transducer comprises a resistive heating transducer.

37. The apparatus of claim 22 wherein said therapeutic transducer comprises:
a first ultrasonic transducer having an acoustic radiating surface, a first electrode and a second electrode each coupled to said first ultrasonic transducer, said first ultrasonic transducer coupled to a first wall of said endoluminal implant; and
a second ultrasonic transducer having an acoustic radiating surface, a first electrode and a second electrode each coupled to said second ultrasonic transducer, said second ultrasonic transducer being coupled to a second wall of said endoluminal implant such that said acoustic radiating surface of said first ultrasonic transducer is aligned with and facing said acoustic radiating surface of said second ultrasonic transducer.

38. The apparatus of claim 22 wherein said therapeutic transducer comprises:
an ultrasonic transducer having an acoustic radiating surface, a first electrode and a second electrode each coupled to said ultrasonic transducer, said ultrasonic transducer coupled to a first wall of said endoluminal implant; and
an acoustic reflector coupled to a second wall of said endoluminal implant, said acoustic reflector being maintained in alignment with and facing said acoustic radiating surface of said ultrasonic transducer.

39. The apparatus of claim 38 wherein said acoustic reflector comprises a magnet.

40. The apparatus of claim 22 wherein said therapeutic transducer comprises an ultrasonic transducer capable of providing collinear acoustic waves at a first frequency and a second frequency.

41. An apparatus configured to be or implanted in a lumen having a passageway, the apparatus comprising:

an endoluminal implant adapted to be implanted within the passageway; and a RF coupling coil integrated in a wall of said endoluminal implant.

42. An apparatus as claimed in claim 41, wherein said RF coupling coil comprises a RF coupling coil chosen from a group comprising: a saddle coil, a helical coil and a woven mesh coil.

43. An apparatus as claimed in claim 41, further comprising a therapeutic transducer electrically coupled to said RF coupling coil.

44. An apparatus as claimed in claim 41, further comprising:

an implantable electronic circuit coupled to said RF coupling coil, said implantable electronic circuit exchanging data, power and control signals with said RF coupling coil; and a therapeutic transducer electrically coupled to said implantable electronic circuit and mechanically coupled to said endoluminal implant, said therapeutic transducer supplying energy to a lumen of said endoluminal implant in response to signals from said implantable electronic circuit.

45. The apparatus of claim 44, further comprising an implantable IC sensor physically coupled to said endoluminal implant and electrically coupled to said implantable electronic circuit.

46. The apparatus of claim 45, wherein said implantable IC sensor provides electrical signals to said implantable electronic circuit that are indicative of a diagnostic parameter associated with a fluid flowing through said lumen, wherein said diagnostic parameter is chosen from a group comprising: fluid flow, pressure, temperature and biochemical information.

* * * * *

UNITED STATES PATENT AND TRADEMARK OFFICE
CERTIFICATE OF CORRECTION

PATENT NO. : 6,231,516 B1 Page 1 of 1
DATED : May 15, 2001
INVENTOR(S) : George W. Keilman and George E. Cimochowski It is certified that error appears in the above-identified patent and that said Letters Patent is hereby corrected as shown below:

<u>Column 45, claim 17,</u>
Lines 9 and 10, "coupling coil; and" should read -- coupling coil and --.

Signed and Sealed this

Thirtieth Day of October, 2001

Attest:

NICHOLAS P. GODICI
Attesting Officer *Acting Director of the United States Patent and Trademark Office*